US007954502B2

(12) United States Patent
Townsend et al.

(10) Patent No.: US 7,954,502 B2
(45) Date of Patent: Jun. 7, 2011

(54) MOBILITY ASSISTANCE APPARATUS

(75) Inventors: Barry W. Townsend, Bakersfield, CA (US); Byron K. Claudino, Bakersfield, CA (US)

(73) Assignee: Bioquest Prosthetics, LLC, Bakersfield, CA (US)

( * ) Notice: Subject to any disclaimer, the term of this patent is extended or adjusted under 35 U.S.C. 154(b) by 1172 days.

(21) Appl. No.: 11/643,677

(22) Filed: Dec. 22, 2006

(65) Prior Publication Data

US 2007/0106397 A1 May 10, 2007

Related U.S. Application Data

(63) Continuation-in-part of application No. 11/411,133, filed on Apr. 26, 2006, now abandoned, which is a (Continued)

(51) Int. Cl.
*A61H 3/02* (2006.01)
*A61F 2/66* (2006.01)
(52) U.S. Cl. ............... 135/82; 135/66; 135/69; 135/84; 623/49; 623/55
(58) Field of Classification Search ............. 135/65–66, 135/68–71, 72, 77, 82, 84; 623/29, 32, 46–47, 623/49–55, 38
See application file for complete search history.

(56) References Cited

U.S. PATENT DOCUMENTS 127,028 A 5/1872 Crandall
(Continued)

FOREIGN PATENT DOCUMENTS

DE 299 20 434 U1 4/2000
(Continued)

OTHER PUBLICATIONS

Canadian Office Action dated Feb. 16, 2009; Application No. 2,446,768; 3 pages; Owner: Barry W. Townsend, et al.; Title: Prosthetic Foot With Tunable Performance.
(Continued)

*Primary Examiner* — Winnie Yip
(74) *Attorney, Agent, or Firm* — Antonelli, Terry, Stout & Kraus, LLP.

(57) ABSTRACT

An improved mobility assistance apparatus for use by a person as a walking aid, e.g. a cane, crutch, or walker, has a support capable of bearing vertical forces during use of the apparatus as a walking aid and a resilient device connected to a lower portion of the support for ground engagement. The device has a dynamic response characteristic to forces associated with ambulating using the apparatus as a walking aid which generates propulsive force to aid mobility. Two coiled springs are monolithically formed with the device at an upper end thereof. A flexible elongated member is connected to a radially inner, free end of each of the coiled springs and extends about a return at a lower portion of the device for resiliently expanding the coiled springs to store energy with force loading of the apparatus during use and to release stored energy during force unloading to generate propulsive force to aid mobility. The dorsiflexion moment of the resilient device is an order of magnitude greater than a plantarflexion moment thereof to mimic human ankle joint function.

20 Claims, 20 Drawing Sheets

Related U.S. Application Data continuation-in-part of application No. 10/915,724, filed on Aug. 11, 2004, now Pat. No. 7,735,501, which is a continuation-in-part of application No. 10/814,260, filed on Apr. 1, 2004, now Pat. No. 7,611,543, and a continuation-in-part of application No. 10/814,155, filed on Apr. 1, 2004, now Pat. No. 7,410,503, which is a continuation-in-part of application No. 10/263,795, filed on Oct. 4, 2002, now Pat. No. 7,226,485, which is a continuation of application No. 09/820,895, filed on Mar. 30, 2001, now Pat. No. 6,562,075, application No. 11/643,677, which is a continuation-in-part of application No. 10/473,682, filed as application No. PCT/US02/09589 on Mar. 29, 2002, now Pat. No. 7,507,259, which is a continuation-in-part of application No. 09/820,895, filed on Mar. 30, 2001, now Pat. No. 6,562,075, application No. 11/643,677, which is a continuation-in-part of application No. 10/529,220, filed as application No. PCT/US02/30471 on Sep. 26, 2002, now Pat. No. 7,374,578, which is a continuation-in-part of application No. 09/820,895, filed on Mar. 30, 2001, now Pat. No. 6,562,075, application No. 11/643,677, which is a continuation-in-part of application No. PCT/US2005/011291, filed on Apr. 1, 2005, and a continuation of application No. 10/814,155, and a continuation-in-part of application No. 10/814,260, application No. 11/643,677, which is a continuation-in-part of application No. PCT/US2005/011304, filed on Apr. 1, 2005.

(60) Provisional application No. 60/558,119, filed on Apr. 1, 2004, provisional application No. 60/558,119, filed on Apr. 1, 2004.

(56) References Cited

U.S. PATENT DOCUMENTS

| | | | | |
|---|---|---|---|---|
| 241,226 | A | 5/1881 | Landis | |
| 267,680 | A | 11/1882 | Crandall | |
| 1,254,061 | A | 1/1918 | Mueller | |
| 1,277,009 | A | 8/1918 | Weldon | |
| 2,453,969 | A | 11/1948 | Carter | |
| 3,040,757 | A | 6/1962 | Smith | |
| 3,738,674 | A | 6/1973 | Pauls | |
| 3,948,535 | A | 4/1976 | Negi | |
| 4,098,283 | A | 7/1978 | Tritle, Jr. | |
| 4,237,915 | A | 12/1980 | Zabielski et al. | |
| 4,411,284 | A | 10/1983 | Opitz | |
| 4,493,334 | A | 1/1985 | Semanchik et al. | |
| 4,708,154 | A | 11/1987 | Edwards | |
| 4,884,587 | A | 12/1989 | Mungons | |
| 4,899,771 | A | 2/1990 | Wilkinson | |
| 4,911,724 | A | 3/1990 | Fikes | |
| 5,116,384 | A | 5/1992 | Wilson et al. | |
| 5,139,525 | A | 8/1992 | Kristinsson | |
| 5,156,632 | A * | 10/1992 | Wellershaus | 623/55 |
| 5,167,746 | A | 12/1992 | Sheenan | |
| 5,224,506 | A | 7/1993 | Allen et al. | |
| 5,301,704 | A | 4/1994 | Brown | |
| 5,331,989 | A | 7/1994 | Stephens | |
| 5,335,683 | A | 8/1994 | Ledley | |
| 5,353,825 | A | 10/1994 | Davis | |
| 5,376,139 | A * | 12/1994 | Pitkin | 623/51 |
| 5,387,246 | A | 2/1995 | Phillips | |
| 5,409,029 | A | 4/1995 | Davis | |
| 5,458,656 | A | 10/1995 | Phillips | |
| 5,465,745 | A | 11/1995 | Davis | |
| 5,509,936 | A | 4/1996 | Rappoport et al. | |
| 5,651,792 | A | 7/1997 | Telikicherla | |
| 5,653,767 | A * | 8/1997 | Allen et al. | 623/52 |
| 5,653,768 | A | 8/1997 | Kania | |
| 5,695,527 | A * | 12/1997 | Allen | 623/55 |
| 5,766,265 | A | 6/1998 | Phillips | |
| 5,829,463 | A | 11/1998 | Galan | |
| 5,897,594 | A | 4/1999 | Martin et al. | |
| 5,954,075 | A | 9/1999 | Gilmour | |
| 6,085,766 | A | 7/2000 | Geary | |
| 6,155,998 | A | 12/2000 | Gilmour | |
| 6,280,479 | B1 | 8/2001 | Phillips | |
| 6,361,515 | B1 | 3/2002 | Gilmour | |
| 6,494,919 | B1 | 12/2002 | Matthews | |
| 6,514,293 | B1 | 2/2003 | Jang et al. | |
| 6,562,075 | B2 | 5/2003 | Townsend et al. | |
| 6,634,608 | B2 | 10/2003 | Jacobowitz | |
| 7,360,547 | B2 | 4/2008 | Carlson | |
| 2001/0001959 | A1 | 5/2001 | Iwasa | |
| 2001/0027802 | A1 | 10/2001 | McGrath | |
| 2002/0087216 | A1 | 7/2002 | Atkinson et al. | |
| 2002/0133237 | A1 | 9/2002 | Christesen | |
| 2002/0144430 | A1 | 10/2002 | Schmid | |
| 2002/0144723 | A1 | 10/2002 | Zulla et al. | |
| 2003/0009238 | A1 | 1/2003 | Whayne | |
| 2003/0028256 | A1 | 2/2003 | Townsend et al. | |
| 2003/0045944 | A1 | 3/2003 | Mosler et al. | |
| 2003/0120354 | A1 | 6/2003 | Doddroe et al. | |
| 2005/0016572 | A1 | 1/2005 | Townsend et al. | |

FOREIGN PATENT DOCUMENTS

| | | |
|---|---|---|
| FR | 2734151 | 11/1996 |
| GB | 2425253 A | 10/2006 |
| JP | 08206165 A | 8/1996 |
| JP | 2003153716 A | 5/2003 |
| WO | WO 99/52476 | 10/1999 |

OTHER PUBLICATIONS

European Office Action dated Apr. 3, 2009; Application No. 02 733 905.0-2310; 4 pages; Applicant: Barry W. Townsend, et al.

International Search Report; International Filing Date: Apr. 26, 2006; International Application No. PCT/US06/15627. Report mailed Sep. 24, 2007.

Written Opinion of the International Search Authority; International Filing date: Apr. 26, 2006; International Application No. PCT/US06/15627.

International Search Report; PCT/US05/11304; Filing Date: Apr. 1, 2005.

International Search Report; PCT/US05/11291; Filing Date: Apr. 1, 2005.

* cited by examiner

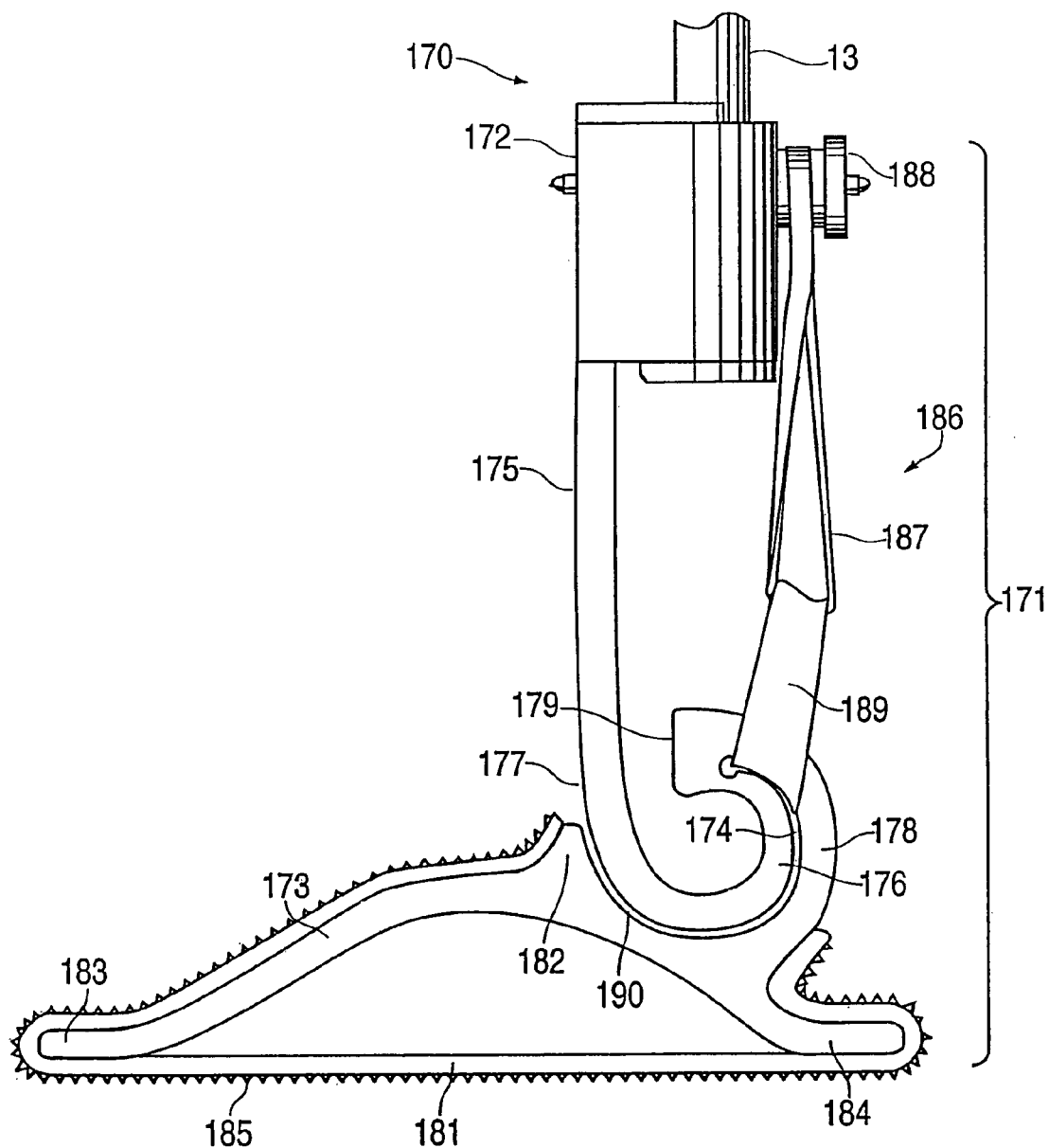

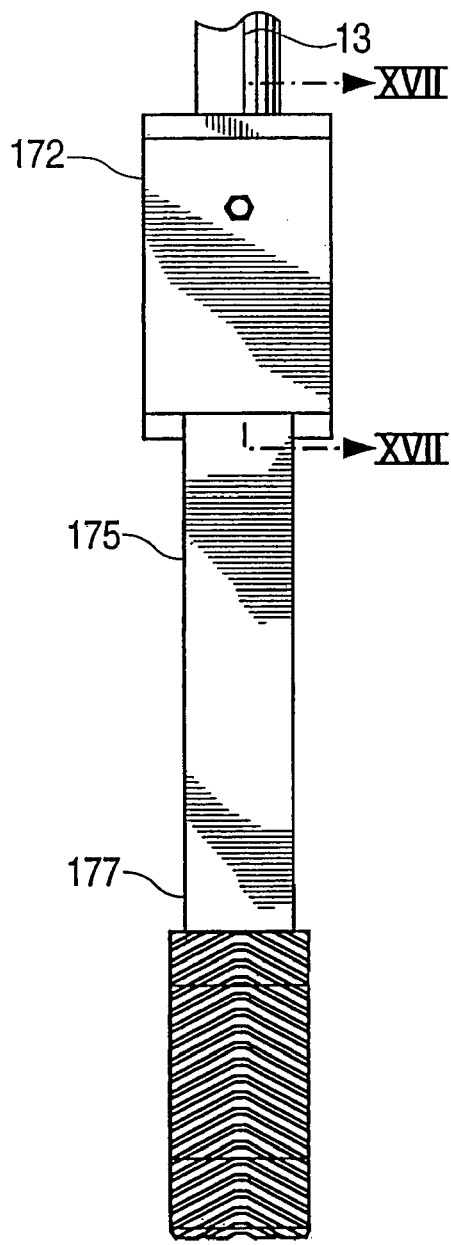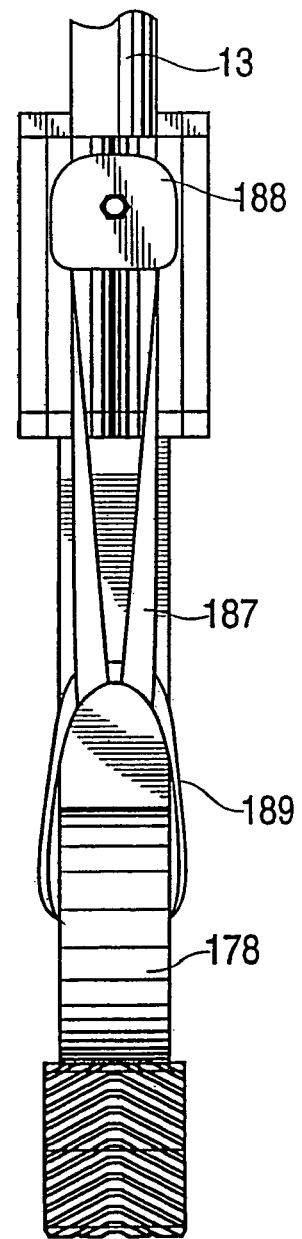

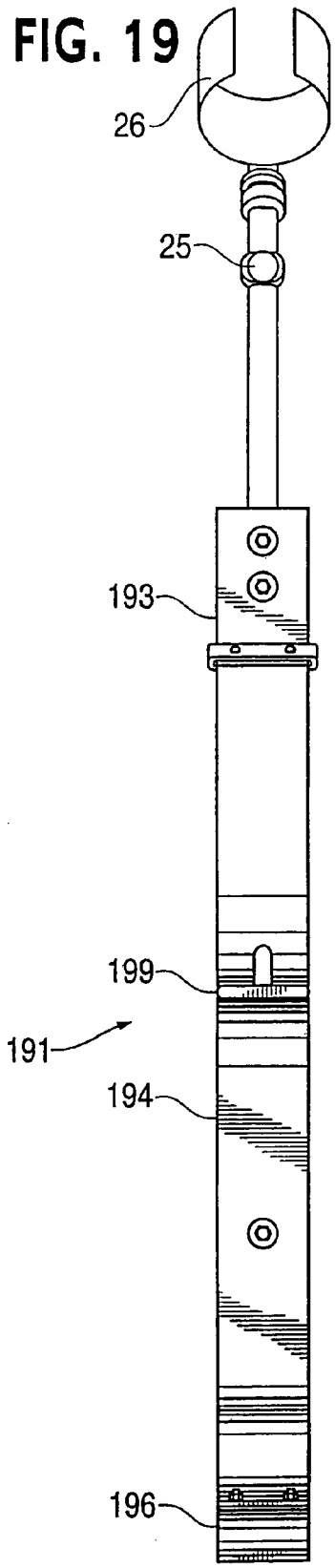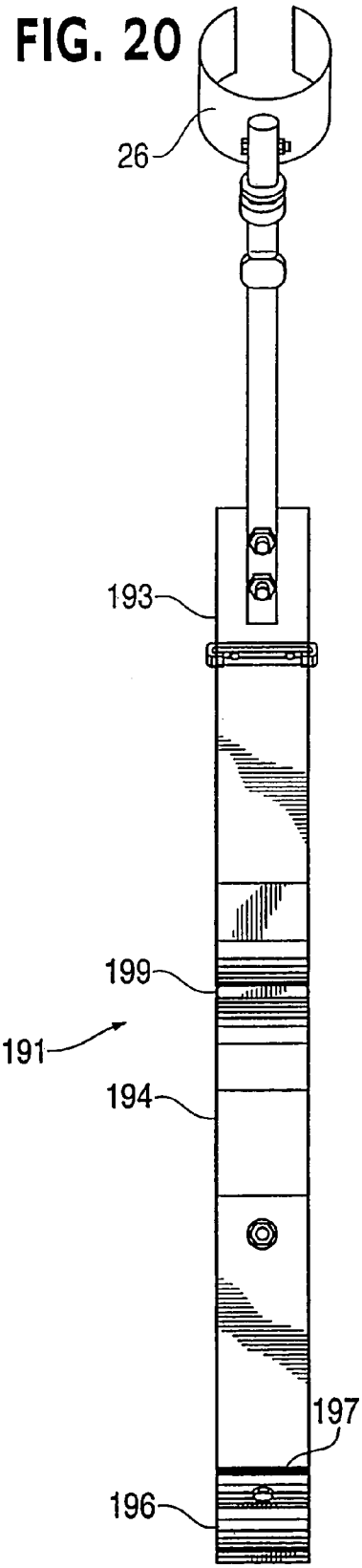

MOBILITY ASSISTANCE APPARATUS

RELATED APPLICATIONS

This application is a continuation in part of application Ser. No. 11/411,133, filed Apr. 26, 2006, and now abandoned, which in turn is a continuation in part of application Ser. No. 10/915,724 filed Aug. 11, 2004, now U.S. Pat. No. 7,735,501 issued Jun. 15, 2010, which is a continuation in part of application Ser. Nos. 10/814,260 and 10/814,155 each filed Apr. 1, 2004, now respectively U.S. Pat. No. 7,611,543 issued Nov. 3, 2009, and U.S. Pat. No. 7,410,503 issued Aug. 12, 2008, which in turn are continuation in part applications of Ser. No. 10/263,795 filed Oct. 4, 2002, now U.S. Pat. No. 7,226,485 issued Jun. 5, 2007, which is a continuation of application Ser. No. 09/820,895 filed Mar. 30, 2001, now U.S. Pat. No. 6,562,075 issued May 13, 2003.

This application is a continuation in part of application Ser. No. 10/473,682 file Sep. 30, 2003, now U.S. Pat. No. 7,507,259 issued Mar. 24, 2009, which is a U.S. national phase application under §371 of International Application No. PCT/US02/09589 filed Mar. 29, 2002, which is a continuation in part of application Ser. No. 09/820,895 filed Mar. 30, 2001, now U.S. Pat. No. 6,582,075 issued May 13, 2003.

This application is a continuation in part of application Ser. No. 10/529,220 file Mar. 25, 2005, now U.S. Pat. No. 7,374,578 issued May 20, 2008, which is a U.S. national phase application under §371 of International Application No. PCT/US02/30471 filed Sep. 26, 2002, which is a continuation in part of application Ser. No. 09/820,895 filed Mar. 30, 2001, now U.S. Pat. No. 6,582,075 issued May 13, 2003.

This application is a continuation in part of International Application No. PCT/US05/011291 filed Apr. 1, 2005 and claiming priority of provisional application Ser. No. 60/558,119 filed Apr. 1, 2004 and application Ser. No. 10/814,155 filed Apr. 1, 2004, now U.S. Pat. No. 7,410,503 issued Aug. 12, 2008, and Ser. No. 10/814,260 filed Apr. 1, 2004, and now U.S. Pat. No. 7,611,543 issued Nov. 3, 2009.

This application is a continuation in part of International Application No. PCT/US05/011304 filed Apr. 1, 2005 which claims priority of application Ser. Nos. 60/558,119, 10/814,260, now U.S. Pat. No. 7,611,543 issued Nov. 3, 2009, and 10/814,155, now U.S. Pat. No. 7,410,503 issued Aug. 12, 2008, each filed Apr. 1, 2004.

TECHNICAL FIELD

The present invention is directed to an improved mobility assistance apparatus, particularly a crutch, cane or walker, which aids mobility with ambulation.

BACKGROUND

For over a century crutches and canes have remained virtually unchanged. Modifications to the crutch or cane itself have generally focused on ergonomic improvements in the physical structure versus functional improvements to mobility. As such, modern ambulatory aids continue to suffer from many of the same functional limitations that plagued their predecessors.

An example of an early crutch, in U.S. Pat. No. 127,028 issued May 21, 1872, involves the use of a round rubber tip made of respective layers of rubber and canvas, each exposed at the tip, to prevent the crutch from slipping on a wet surface. The use of a passive curved rocker provided at the lower end of the crutch to increase the progression or ground covered with use of the crutch is taught by U.S. Pat. No. 267,680 issued Nov. 21, 1882. A pneumatic cushion is used to form a curved rocker or bearer at the tip of the crutch in the patent to Mueller, U.S. Pat. No. 1,254,061 issued Jan. 22, 1918. The U.S. Pat. No. 1,277,009 to Weldon, issued Aug. 27, 1918, teaches the use of curved segmental base pieces at the tip of the crutches for ground engagement.

More recently, examples of annular crutch tips with features to resist slipping when engaged with the ground are shown by U.S. Pat. Nos. 3,040,757; 4,098,283; 4,411,284; 4,237,915 and 4,708,154. A radial crutch tip assembly with a base bottom surface and a resilient boot having a shape of a rocker is disclosed by Davis in each of U.S. Pat. Nos. 5,353,825; 5,409,029 and 5,465,745.

In other examples of walking aids, Wilkinson, U.S. Pat. No. 4,899,771, provides a foot member for the walking aid which is curved upwardly at its front and back ends to permit limited rolling of the foot member when used with a cane or crutch during a walking procedure. Similarly, Stephens discloses in U.S. Pat. No. 5,331,989 curving the front, rear and inner sides of the foot member of a walking aid to permit limited rolling of the crutch tip laterally as well as forward and backward.

Galan, in U.S. Pat. No. 5,829,463 provides the crutch tip with a heel portion or extension extending rearwardly from the tip at an upward angle. The heel portion is used to prevent slipping when the user is rising from a seated position. Semanchik et al. disclose in U.S. Pat. No. 4,493,334 a walking aid having a foot pad shaped with a curved sole to simulate an anatomical foot for achieving a rocking movement in use by imitating the phases of a normal gait, i.e. heel strike, foot flat and toe off. A published U.S. patent application, US 2001/0027802 A1 to McGrath, is directed to a walking aid comprising a shaft and a foot assembly, in which the foot assembly includes in combination a sleeve member and a foot member adapted for relative axial sliding movement and including resilient movement-restraint means for alleviating problems from shock loading transferred up the walking aid to the user's hand, wrist, arm and shoulder.

One of the single largest deficiencies of conventional walking assistance devices is the excessive amount of energy needed to stabilize the walking system (the device and the user's body) with the ground, and to efficiently move the user's body through space. In fact, a crutch user expends as much as 2.5 times more energy to move his/her body mass, in space, as compared to an able bodied person. Furthermore, the lack of sufficient surface area at the ground engaging surface of a walking assistance device engenders other dangers such slippage on uneven or slick surfaces. While improvements have been made with respect to the surface area at the point of contact for walking assistance devices, these improvements have been one-dimensional due to the limitations of the designs. It has been found by Applicants that the principal limitation to even the most progressive crutch or cane tip, with respect to surface area and/or surface textures, is the inability of these devices to stabilize the walking system while simultaneously translating the vertical forces associated with crutch/cane ambulation into forward propulsion and mobility. There is a need for an improved mobility assistance apparatus capable of stabilizing the walking system while lessening the user's necessary energy expenditure and discomfort associated therewith. More particularly, there is a need for a low cost, high function mobility assistance apparatus having improved loading response shock absorption and sagittal plane positive kinetic power which is needed for doing the work of walking. There is also a need for such an apparatus which is adaptable for use on different terrain/ground surfaces including ice, snow and mud.

SUMMARY OF INVENTION

An object of the present invention is to address the aforementioned needs. To this end, the present invention is an improved, low cost, high function mobility assistance apparatus which improves the mobility of a person using the apparatus as a walking aid. The apparatus has improved loading response shock absorption and sagittal plane positive kinetic power which is needed for doing the work of walking. An embodiment of the mobility assistance apparatus of the invention comprises a support member capable of bearing vertical forces during use of the support member as a walking aid, and a device connected to a lower portion of the support member for ground engagement. The device includes a resilient foot, ankle and shank which store energy during force loading and release stored energy during force unloading to generate forward propulsive force to aid mobility with ambulation using the apparatus as a walking aid. The ankle and shank are formed by a resilient member having a reversely curved lower end secured to the foot to form the ankle and extending upward from the foot by way of an anterior facing convexly curved portion of the member. The resilient member is secured to the foot by way of a coupling element which houses the reversely curved lower end of the member. With this construction, the apparatus has improved spring efficiency for enhancing loading response shock absorption and sagittal plane positive kinetic power when the apparatus is used as a walking aid during ambulation. The resilient member, coupling element and foot in a preferred form of the invention are monolithically formed, as by extrusion, molding, casting and/or machining, which can lower the manufacturing cost.

The resilient foot of the apparatus in example embodiments has a forefoot portion, an upwardly arched midfoot portion and a hindfoot portion. In one form of the invention, to store additional energy an elastic member extends in spaced relation to the upwardly arched midfoot portion and connects plantar posterior and anterior portions of the foot. The elastic member is elongated during force loading of the apparatus to store energy which is released during force unloading to aid propulsion with ambulation using the apparatus as a walking aid. At least a portion of the distal surface of the elastic member can be formed with tread to serve as a sole of the foot. Alternatively, or additionally, the apparatus can include, in combination, a set of various terrain foot slipper socks each being removably mountable on the resilient foot and having a respective one of a plurality of different distal surface configurations for different ground surfaces. In an example embodiment, slipper socks with distal surface configurations for ice, snow and mud, are provided.

According to another feature of the invention, the support capable of bearing vertical forces during use of the apparatus, is resilient and flexes to store additional energy during force loading and release stored energy during force unloading to aid mobility with ambulation using the apparatus as a walking aid. In a disclosed embodiment, the resilient support is anterior facing convexly curved over at least most of the height of the support, and forms a curvilinear thigh shank connected to an upper end of the shank of the device for ground engagement. A posterior shank device can be employed on at least one of the thigh shank of the support and the shank of the device to store additional energy on expansion of the at least one of the thigh shank and shank of the device under force loading and to release the stored energy during force unloading to aid mobility.

In one form of the invention the posterior shank device includes at least one coiled spring on the shank above the ankle. The coiled spring is resiliently expanded during use of the mobility assistance apparatus by a flexible elongated member connected to a radially inner, free end of the coiled spring and extending over the coiled spring to a lower portion of the device. In a preferred embodiment, two coiled springs of the posterior shank device are cooperatively connected at their radially inner, free ends by a common flexible, elongated member. A low cost high function mobility assistance apparatus can be formed by monolithically forming the coiled springs with the resilient shank, ankle foot and coupling element of the device.

These and other objects, features and advantages of the present invention will be more apparent from a consideration of the following detailed description of disclosed example embodiments of the invention and the accompanying drawings.

BRIEF DESCRIPTION OF DRAWINGS

FIG. 14 is a side view of the lower portion of an additional embodiment of a crutch according to the invention, including a device for ground engagement forming the crutch tip connected by way of an adapter to the lower end of a hollow staff as in the embodiment of FIG. 1.

FIG. 15 is a front view of the mobility assistance apparatus of FIG. 14, as seen from the left side of FIG. 14.

FIG. 16 is a rear view of the crutch of FIG. 14, as seen from the right side of FIG. 14.

FIG. 19 is a front view of the crutch of FIG. 18 as seen from the left side of FIG. 18.

FIG. 20 is a rear view of the crutch of FIG. 18 as seen from the right side of FIG. 18.

DETAILED DESCRIPTION OF EMBODIMENTS

Figure 1:
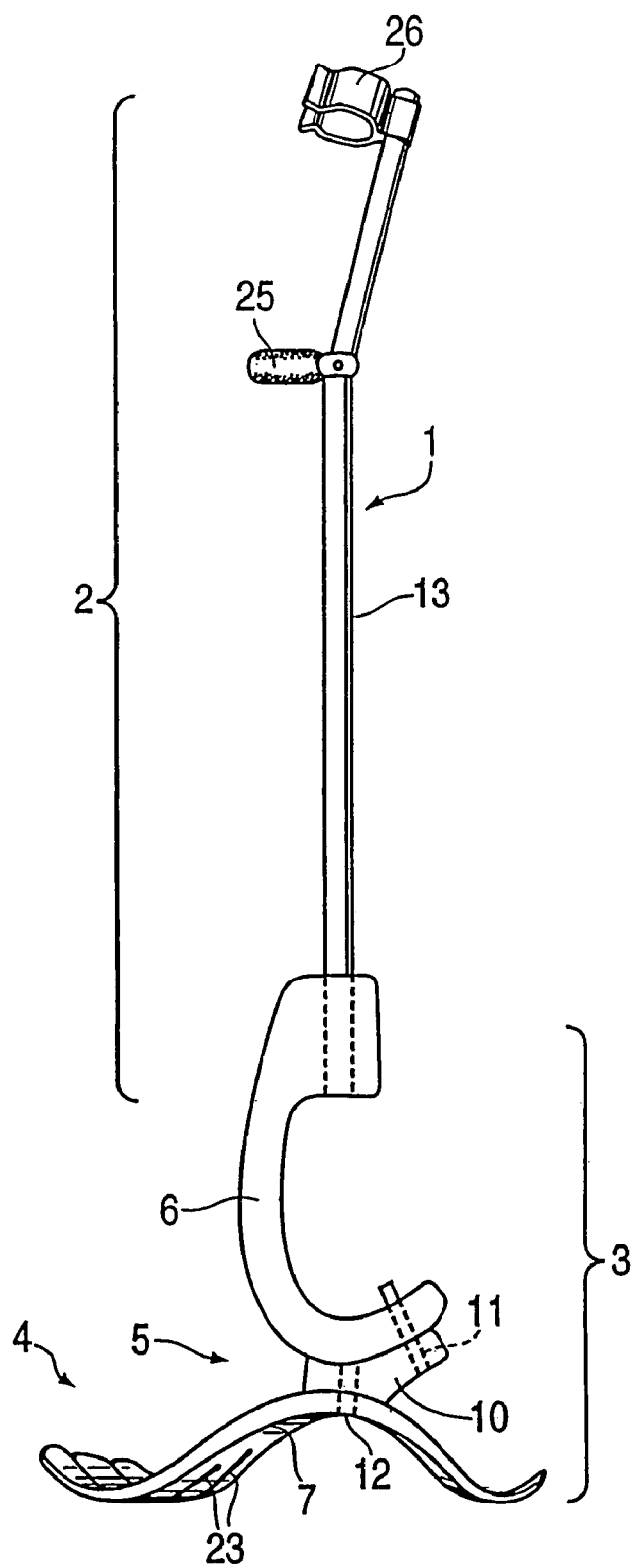
FIG. 1 is a left side view of a mobility assistance apparatus according to an embodiment of the invention.
Figure 2:
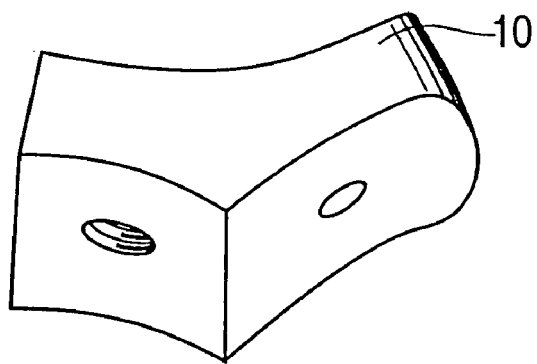
FIG. 2 is an enlarged view from below and to one side of a coupling element of the apparatus of FIG. 1 by which a foot keel and a shank of the apparatus are connected.
Figure 3:
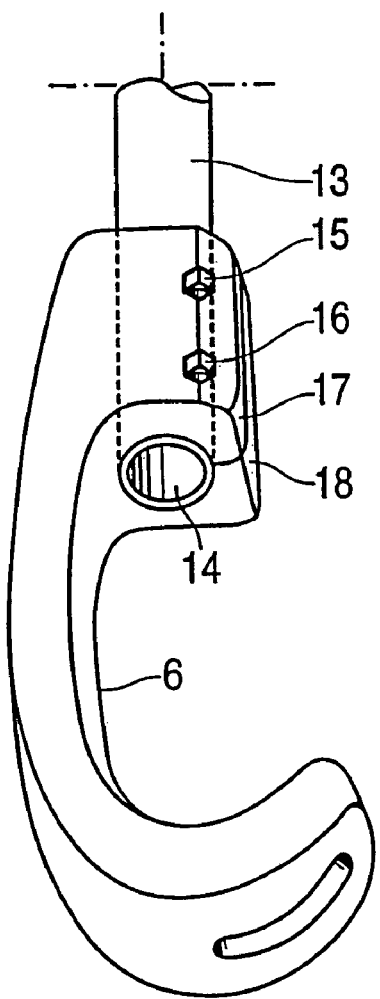
FIG. 3 is an enlarged left side view of a portion of the apparatus of FIG. 1 showing the connection between the lower end of a support member of the apparatus and the upper end of the shank.

Referring now to FIGS. 1-3 of the drawings, a mobility assistance apparatus 1 according to a first embodiment is formed of a walking aid 2 in the form of a forearm crutch and a device 3 connected to a lower portion of the walking aid for ground engagement. The device 3 has a dynamic response characteristic to forces associated with ambulating using the walking aid which generates forward propulsion to aid mobility. The device 3 in the embodiment is a resilient lower extremity prosthesis, e.g. a prosthetic foot, which stores energy during force loading and releases stored energy during force unloading to generate propulsive force. In the example embodiment the device 3 is a prosthesis according to commonly owned U.S. Pat. No. 6,562,075.

The prosthesis 3 includes a resilient foot 4, ankle 5 and calf shank 6. The foot 4 includes a foot keel 7 and optionally a protective covering not shown in FIG. 1 but like covering 8 shown in outline in FIG. 4, for example. The covering 8, which may be formed of rubber, has ridges 9 on the bottom, ground engaging surface thereof to resist slipping during use. If a separate protective covering is not employed on the device 3, ridges or other surface irregularities can be provided directly on the under surface of the foot keel to resist slippage as discussed below.

The shank 6 is connected to the foot keel by way of a coupling element 10 and fasteners 11 and 12 to form the ankle 5 of the prosthesis. At least a lower portion of the shank is anterior facing convexly curved. The foot keel is upwardly arched in its midportion. The adjacent radii of curvatures of the resilient foot keel and calf shank of the prosthesis create a dynamic response capability and motion outcome of the prosthesis in a direction having horizontal and vertical components as explained with reference to FIGS. 1 and 2 of U.S. Pat. No. 6,562,075, to generate a propulsive force during ambulating.

The walking aid 2 of the apparatus 1 is formed with a hollow staff 13 that serves as a support member capable of bearing vertical forces from the weight of the user on the crutch during use as a walking aid. A hand grip 25 and forearm support 26 are mounted on the staff. The length of the staff could be adjustable as by the use of adjustably telescoped staff portions, not shown. While the walking aid 2 in the mobility assistance apparatus 1 is a forearm crutch, other types of walking aids could be used as the walking aid in the apparatus, including another type of crutch, a cane, or a walker, for maximizing functionality and mobility, while lessening the user's necessary energy expenditure and discomfort associated therewith.

The device 3 is preferably capable of sagittal and transverse plane motion in response to forces associated with ambulating using the walking aid. Transverse plane motion, provided for example by the provision of longitudinally extending expansion joints 23 in the foot keel as disclosed in related U.S. Pat. No. 6,562,075 and/or by the use of a coupling element permitting motion of the foot about a joint axis which is at least primarily in the frontal and transverse planes as shown in FIGS. 28-35 of commonly owned related U.S. patent application Ser. No. 10/473,465, ensures, together with sagittal plane motion capability, that the bottom surface of the foot keel will remain parallel to the ground, maintaining maximum contact and traction throughout the ambulatory cycle. The energy storing prosthetic foot 3 is capable of enhancing and/or replicating the propulsion that an individual would experience at the foot, ankle, and calf during the gait cycle, if uninjured or able bodied.

Figure 4:
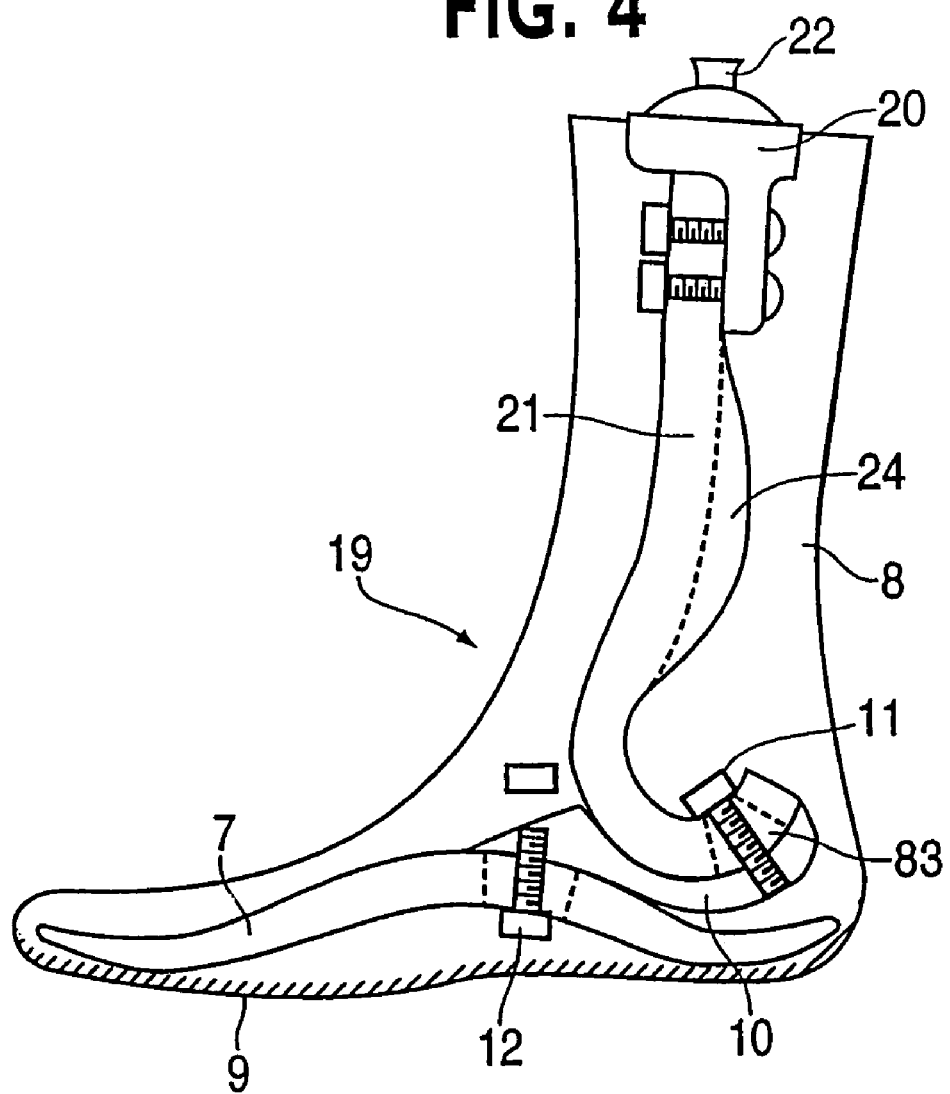
FIG. 4 is a left side view of another form of a resilient lower extremity prosthesis for use in the apparatus of FIG. 1, the prosthesis having an outer protective covering, shown in outline, the covering having a slip resistant lower surface for ground engagement, a male pyramid connector of a male/female pyramid connection system being shown for connecting the prosthesis to a lower end of a supporting member of the apparatus.

In the absence of a protective covering on the prosthesis 3 as shown in FIG. 4, a rubber surface or a compressible foam surface is preferably bonded to the underside of the foot keel 7 using an epoxy glue, for example. The rubber or foam surface is preferably provided with a slip resistant/traction characteristic. For example, corrugated vanes could be formed on the ground engaging rubber or foam surface for increased traction over wet surfaces. In addition, or alternatively, a boot which fits over the entire body of the prosthetic foot keel, excluding the shank, can be used to achieve variable traction needs, the bottom surface of the boot being provided with a slip resistant surface, e.g. cleats, ridges, etc.

The releasable connection between the lower end of staff 13 and the upper end of shank 6 in the apparatus 1 is shown in the enlarged view of FIG. 3. The upper end of the shank is formed with an elongated opening 14 for receiving the lower end of staff 13. Once received in the opening, the staff is securely clamped to the shank by tightening bolts 15 and 16 to draw the free side edges 17 and 18 of the shank along the opening together. This connection can be readily adjusted by loosening the bolts, telescoping the staff relative to the shank to the desired position and reclamping the staff in the adjusted position by tightening the bolts.

The connection between the prosthesis and the walking aid/support member is not limited to that shown in the example embodiment of FIGS. 1-3. Other types of connections including a conventional male/female pyramid system, for example, could be employed. The prosthetic foot 19 in FIG. 4, for use in a mobility assistance apparatus of the invention, has an adapter 20 bolted to the upper end of the shank 21. The adapter 20 has a male pyramid 22 thereon for reception in a complementarily shaped socket of an adapter provided on the lower end of staff 13.

The device 3 according to the invention may be formed from acetal homopolymer or copolymer (Delrin/Celcon), for example, or other materials including aluminum, carbon or graphite composites, glass, and/or Kevlar. In the preferred embodiment the device 3 is formed of acetal plastic, by either machining or injection molding.

The prosthetic foot 19 in FIG. 4 is similar to that in FIG. 1 although the shank 21 thereof is reversely curved on itself above an anterior convexly curved lower portion. Fins 24 are formed on the posterior side of the reversely curved portion of the shank to alter the flexing characteristic of the shank as discussed with respect to FIGS. 28-32 of commonly owned related U.S. patent application Ser. No. 10/473,680.

The device 3 of the invention is not limited to the two examples of FIGS. 1 and 4. Other devices, particularly lower extremity prostheses/prosthetic feet capable of storing and releasing energy during use to generate propulsion could be used in the mobility assistance apparatus and method of the invention for stabilizing the walking system and lessening the user's necessary expenditure of energy and discomfort associated therein. Examples of additional prostheses for use in the mobility assistance apparatus of the invention are shown in FIGS. 5-28. These prostheses are relatively inexpensive in that they can be monolithically formed as by injection molding acetal plastic or by extrusion or other methods as disclosed herein. The resulting mobility assistance apparatus employing the prosthesis is able to create power for enhancing mobility yet is low cost.

Figure 5:
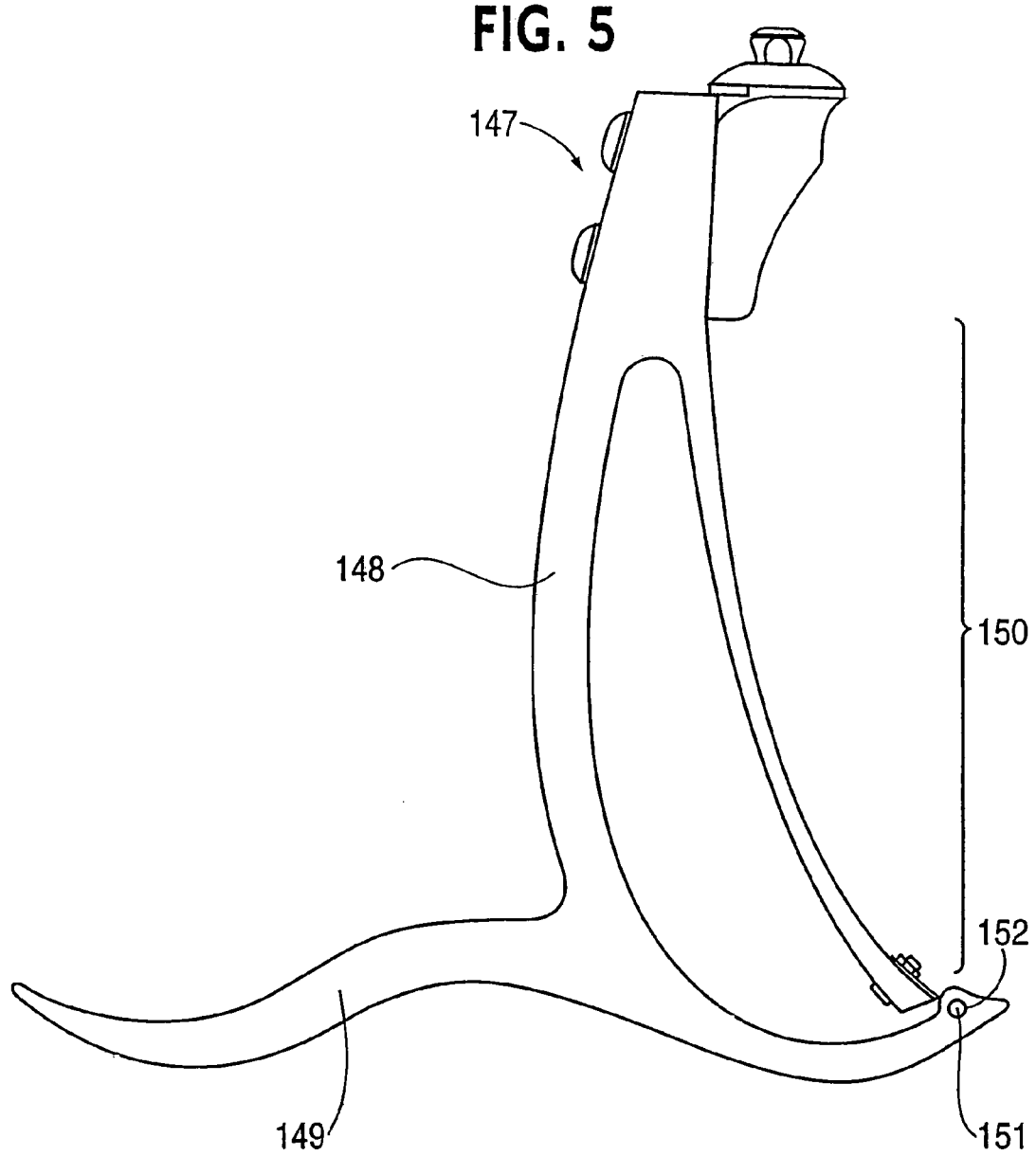
FIG. 5 is a side view of another embodiment of a prosthetic foot for use in the mobility assistance apparatus, wherein the calf shank and foot keel and also a posterior calf device of the prosthesis are monolithically formed, the distal end of a spring of the posterior calf device being pivotably connected to the posterior of the foot keel.
Figure 6:
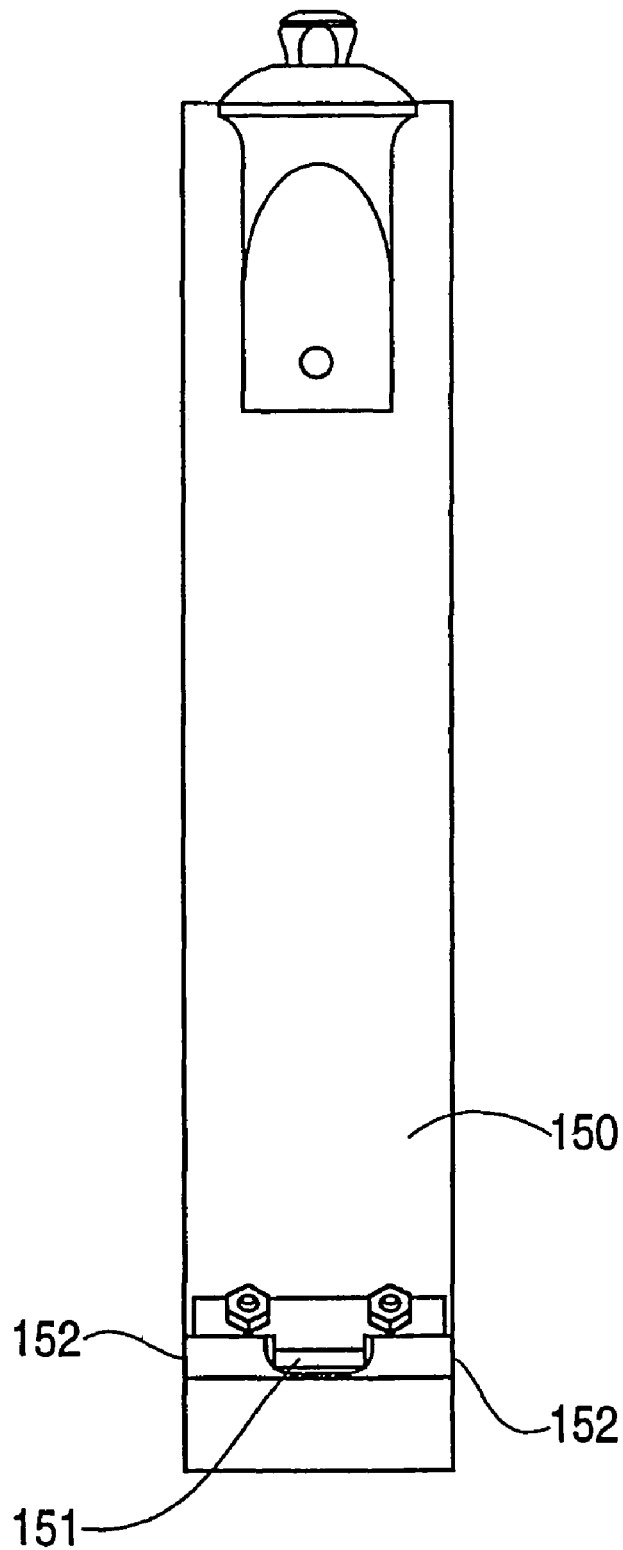
FIG. 6 is a rear view of the prosthesis of FIG. 5.
Figure 7:
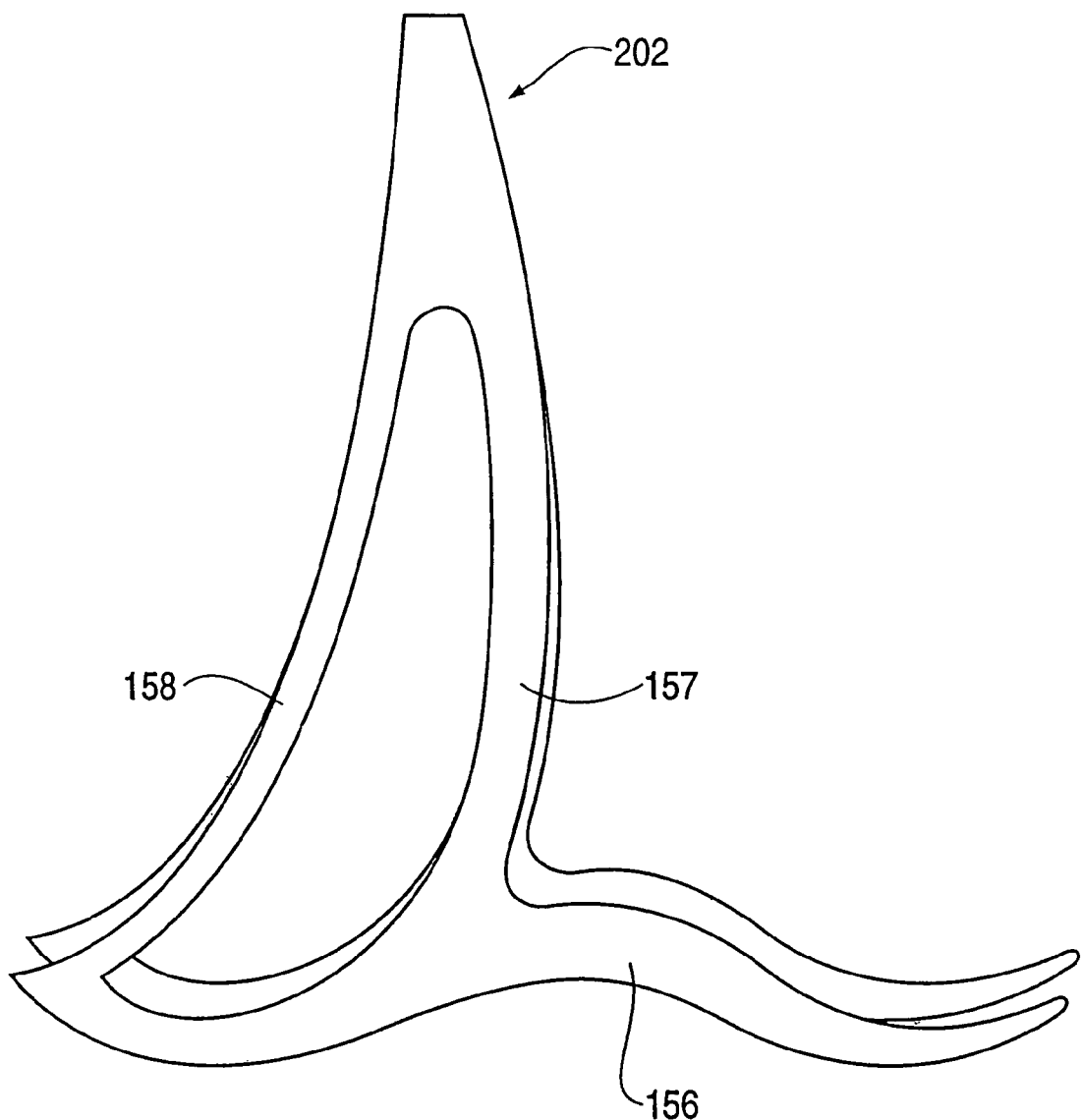
FIG. 7 is a side view of another example of a prosthetic foot similar to that of FIGS. 5 and 6 for use in the mobility assistance apparatus, but where the foot keel, calf shank and posterior calf device are monolithically formed with three, side by side longitudinal sections freely movable with respect to one another at their distal ends but connected at the proximal end of the calf shank, with the center section being wider, and at its distal surface higher, than the outer sections.
Figure 8:
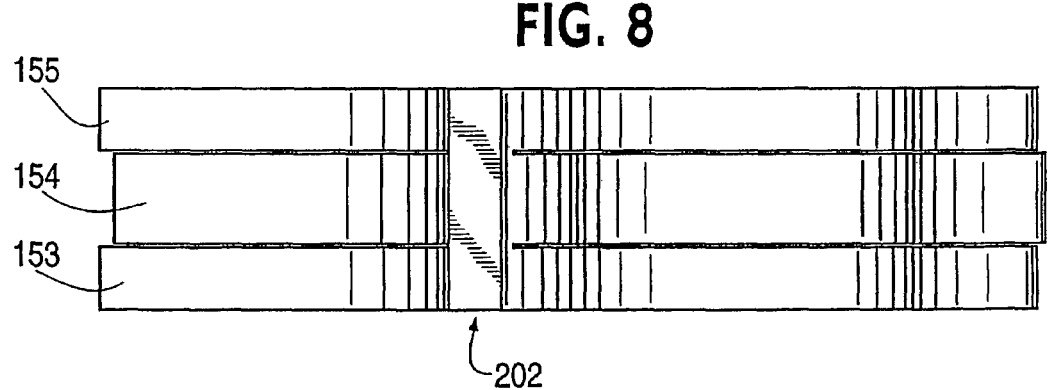
FIG. 8 is a top view of the prosthesis of FIG. 7.
Figure 9:
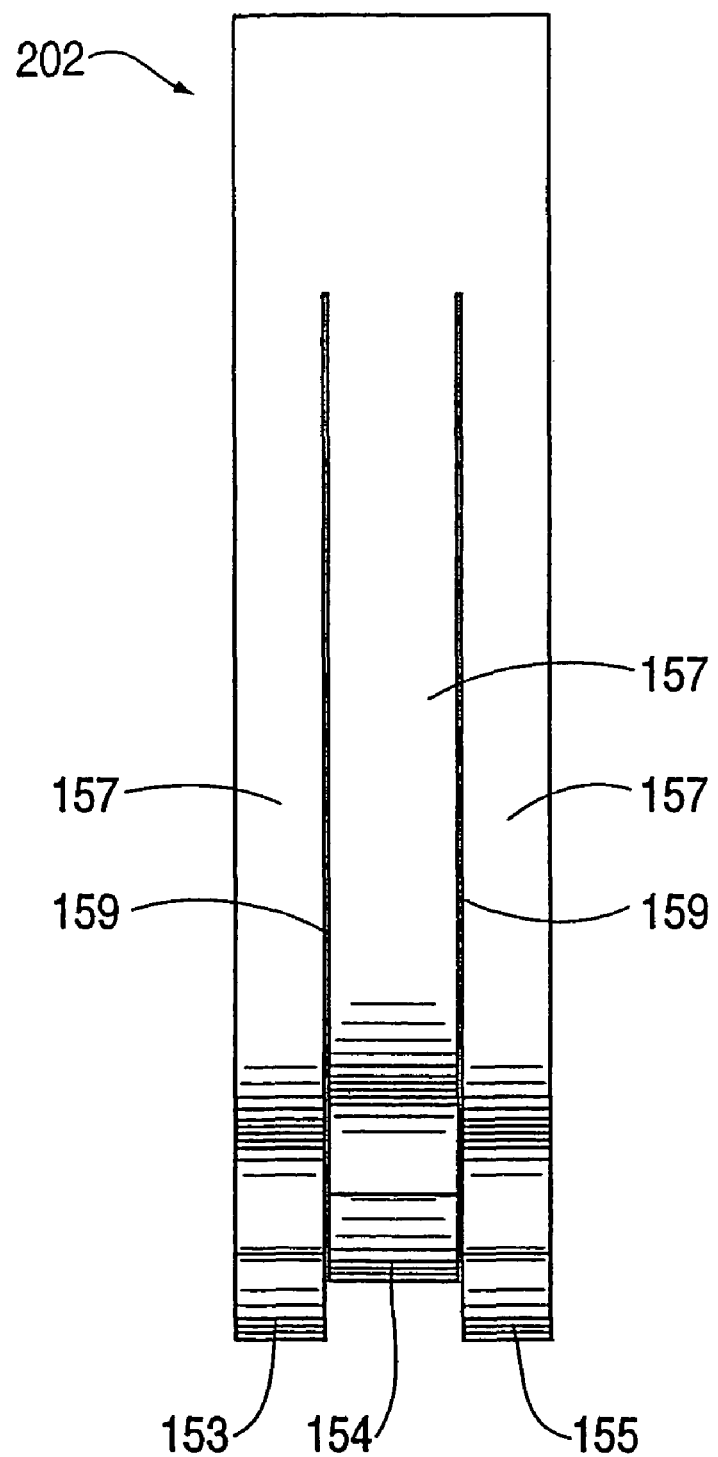
FIG. 9 is a front view of the prosthesis of FIGS. 7 and 8.
Figure 10:
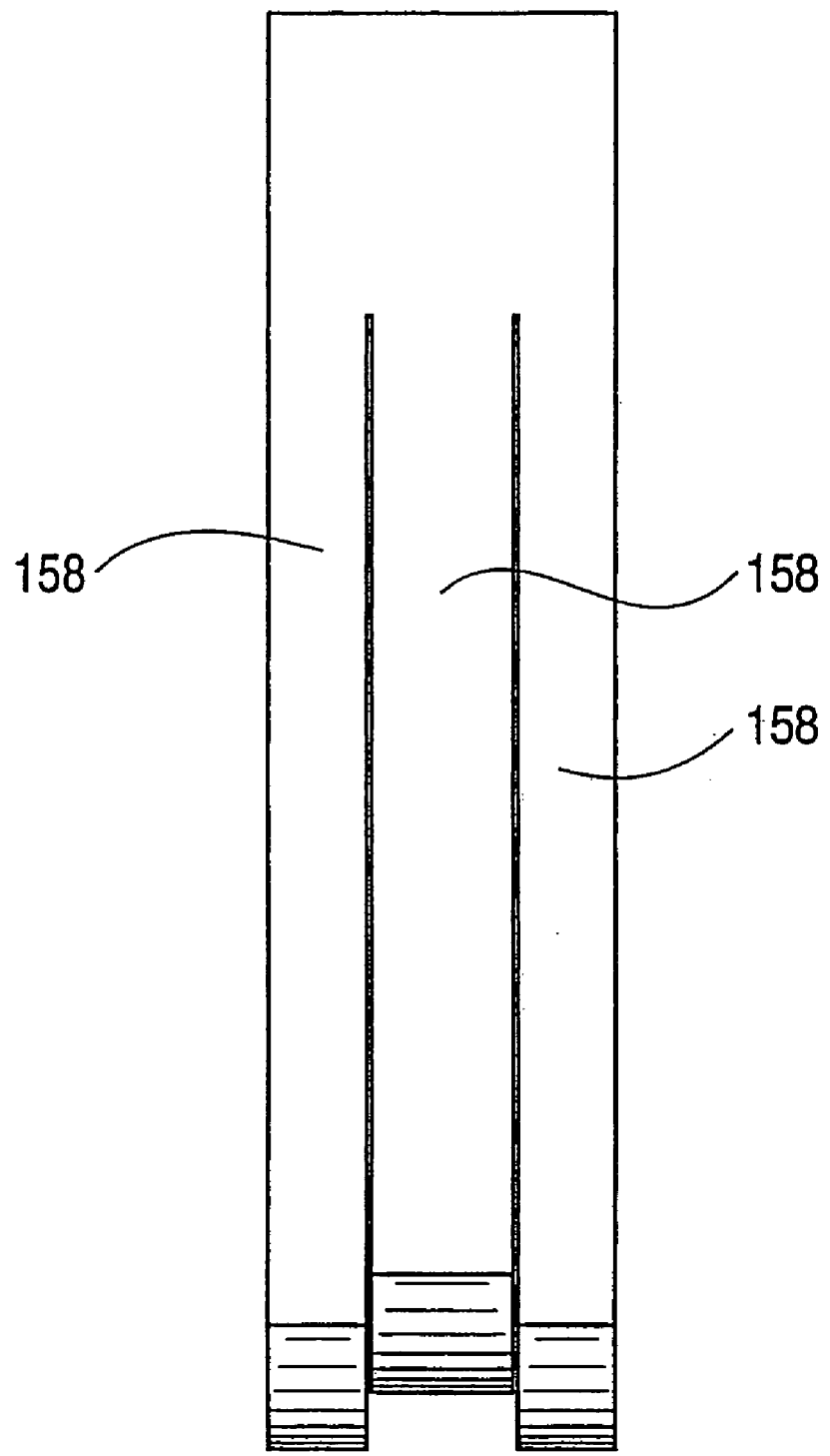
FIG. 10 is a rear view of the prosthesis of FIGS. 7-9.

The prosthetic foot 147 of FIGS. 5 and 6 is characterized by a calf shank 148, foot keel 149 and posterior calf device 150 which are monolithically formed. The calf shank 148 has an anterior facing convexly curved lower portion extending upwardly from the foot keel as in previously described prostheses. The posterior calf device 150 is in the form of an elongated, resilient, curved spring connected at its proximal end to an upper portion of the calf shank and at its distal end the spring is pivotably connected to a posterior portion of the foot keel by a bracket with pivot pin 151 mounted on the distal end of the spring with the pin extending through apertures 152 in the posterior end of the foot keel. The ends of pin 151 are anchored in the openings 152 in the foot keel as shown in the drawings. With anterior or posterior motion of the upper end of the calf shank in gait with the mobility assistance apparatus of the invention, the concavity of the curved spring will be expanded or compressed to store energy within the motion limits of the spring. The stored energy will then be returned upon force unloading in gait to add to the kinetic power available for propulsive force of the user's body.

The prosthesis in FIGS. 7-10 is a prosthetic foot 202 having three longitudinal sections 153-155. Each longitudinal section is monolithically formed with a foot keel 156, calf shank 157 and posterior calf device 158. The sections 153-155 are movable independent of one another at their distal ends, where they are separated by gaps 159, but the sections are integral at their proximal ends, e.g. at the upper end of the calf shank. This integral construction can be provided by use of fasteners for connecting the proximal ends of the respective, separately formed longitudinal sections to one another. Alternatively, the resilient longitudinal sections can be monolithically formed with one another such that they are connected at their upper ends while freely movable relative to each other at their distal ends where gaps 159 separate the sections.

The center longitudinal section 154 in the prosthesis 152 is wider than the medial and lateral sections 153 and 155 and also, at its distal end, it is higher than the sections 153 and 155. This construction provides advantages in support on uneven or inclined surfaces as discussed previously in connection with the use of a plurality of longitudinal anterior and posterior foot keel struts separated by expansion joints. The number of the plurality of longitudinal sections employed in the prosthesis can be other than three and the relative widths of the sections can be varied from that shown in FIGS. 7-10. The distal ends of the curved spring of posterior calf device 158 of each longitudinal section is formed integrally with the hindfoot of its foot keel 156 rather than being pivotably connected thereto as in the embodiment of FIGS. 5 and 6. A suitable adapter, not shown, is connected to the upper end of the calf shank of the prosthesis 152 for connection with the support member, hollow shaft 13, of the walking aid 2 to form a mobility assistance apparatus of the invention as described in previous embodiments.

Figure 11:
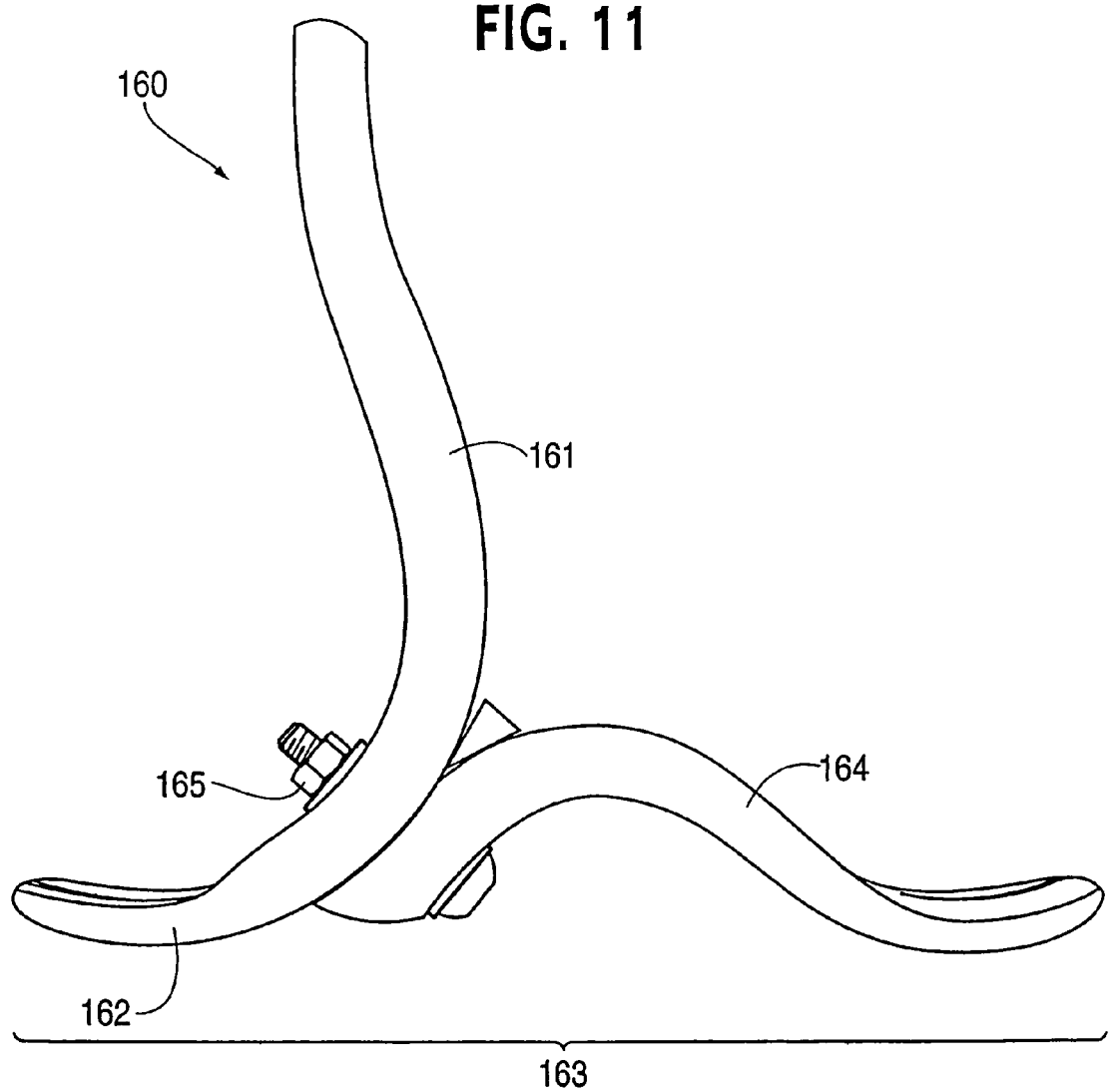
FIG. 11 is a side view of another form of the calf shank and foot keel of a prosthesis for the mobility assistance apparatus of the invention wherein the shank is monolithically formed with a posterior portion of the foot keel, which is connected by fasteners to a forefoot and midfoot forming member of the prosthesis.
Figure 12:
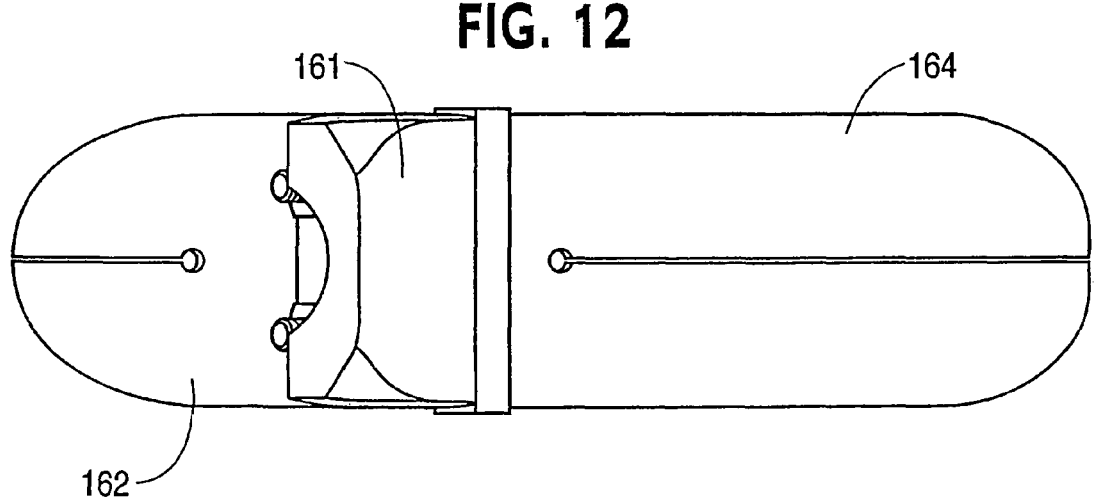
FIG. 12 is a top view of the calf shank and foot keel of FIG. 11.
Figure 13:
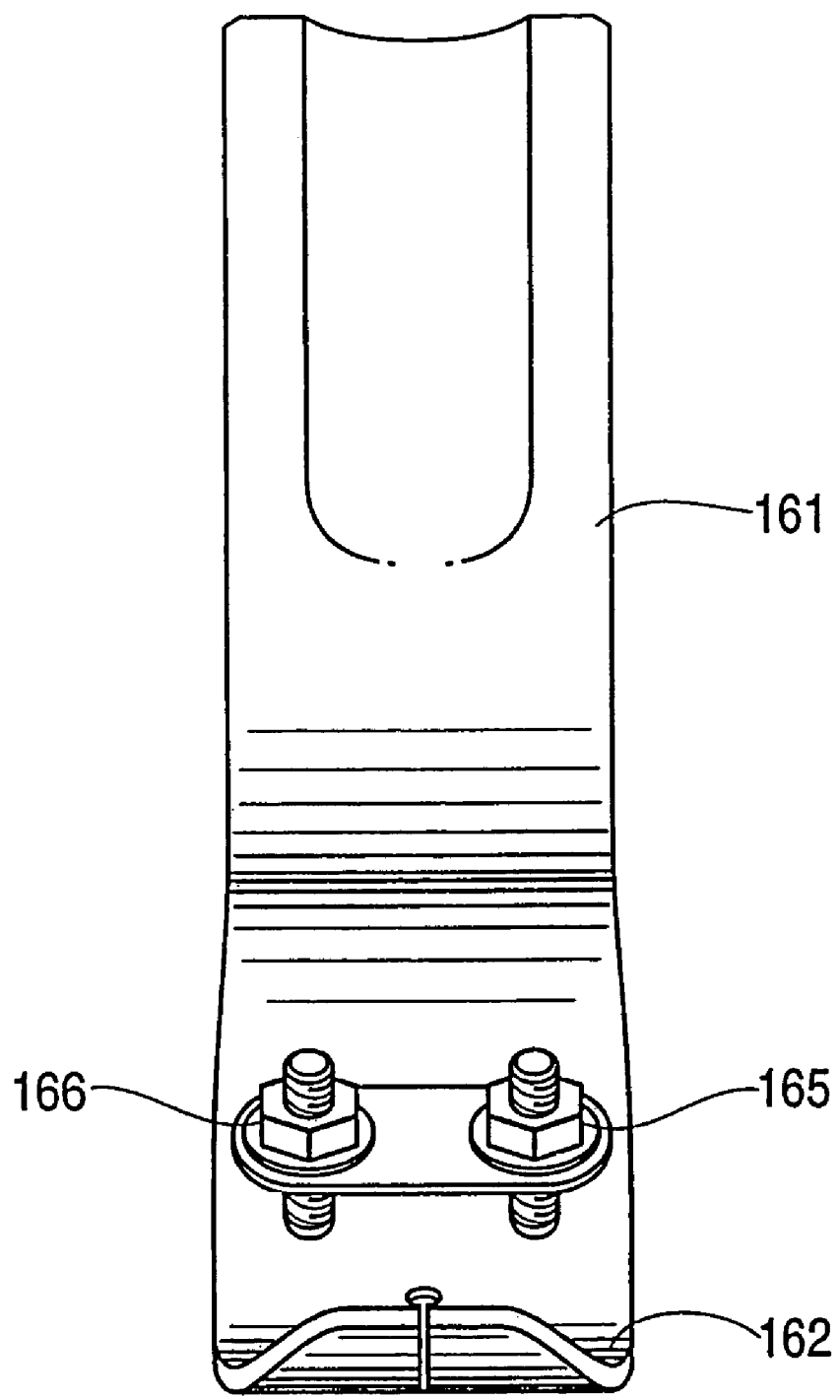
FIG. 13 is a rear view of the calf shank and foot keel of FIGS. 11 and 12.
Figure 17:
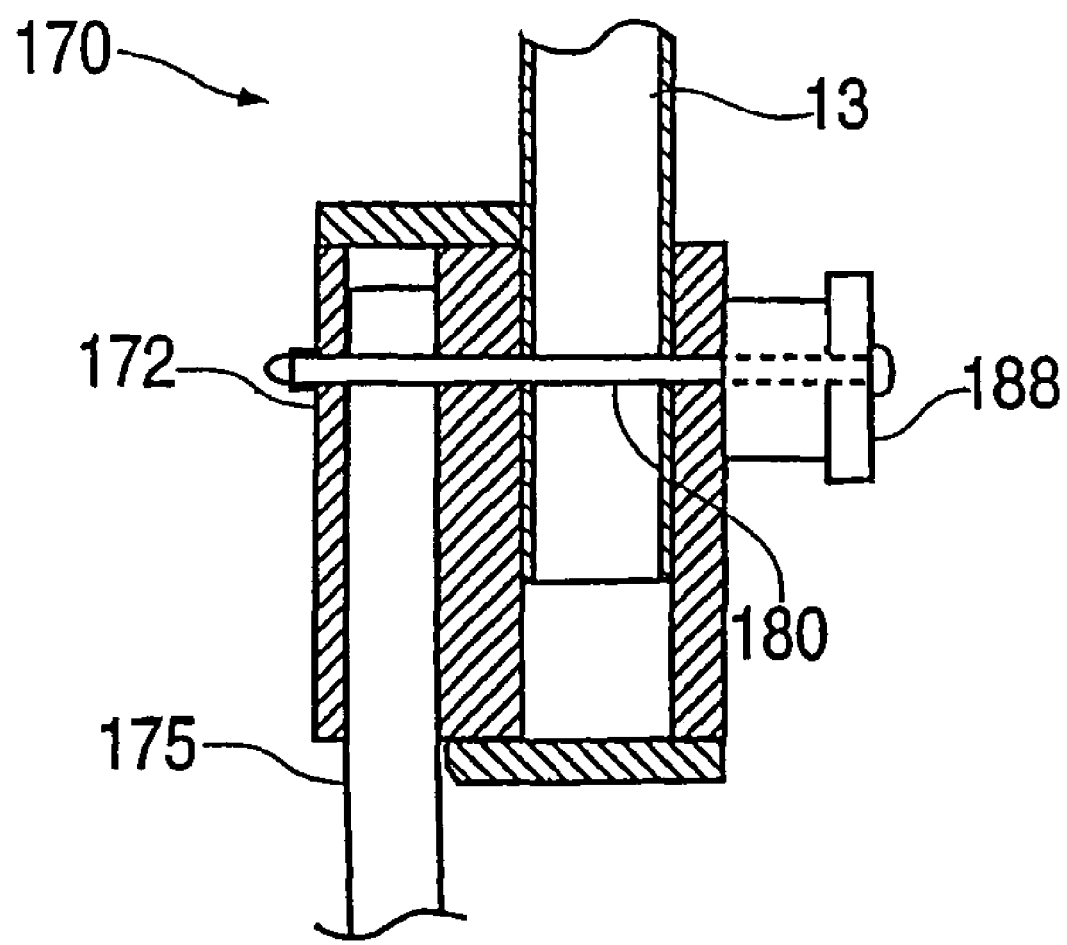
FIG. 17 is a cross sectional view of the adapter of the apparatus of FIGS. 14-16 taken along the line XVII-XVII in FIG. 15.

Another form of construction for the prosthetic foot for use with the invention is illustrated in FIGS. 11-13 wherein the prosthetic foot 160 comprises a calf shank 161 monolithically formed with a posterior portion 162 of foot keel 163. The resilient member of the shank and hindfoot is connected to a resilient member 164 forming forefoot and midfoot portions of the foot keel by fasteners 165 and 166 as shown in the drawings. A posterior calf device, not shown in FIGS. 11-13, can be formed as part of the prosthesis as disclosed above. Likewise, an adapter for connection to a support member of a walking aid is to be attached to the upper end of the calf shank 161.

FIGS. 14-17 depict the lower end of a forearm crutch 170 wherein a device 171 for ground engagement in the form of prosthetic foot is connected to the lower end of a hollow staff 13 of the crutch by way of an adapter 172. The hollow staff at its upper end has a hand grip and forearm support, not shown, like those in the embodiment of FIG. 1. The device 171 includes a resilient foot 173, ankle 174 and shank 175 which, as described above with respect to previous embodiments, flex to store energy during force loading and release stored energy during force unloading to generate forward propulsive force to aid mobility with ambulation using the apparatus 170 as a walking aid. The ankle and shank are formed by a resilient member having a reversely curved lower end 176 secured to the foot to form the ankle and extending upward from the foot by way of an anterior facing convexly curved portion 177 of the member. The resilient member is secured to the foot by way of a coupling element 178 which houses the reversely curved lower end of the member. In the example embodiment, the resilient member, coupling element and foot are preferably monolithically formed by extrusion of a plastic material such as polyurethane. Alternatively, the monolithically formed device 171 could be formed by other methods including molding, machining and/or casting, and using other materials, for example metal to construct the device as discussed above with respect to previous embodiments.

The lower end 176 of the resilient member forming the ankle and shank is reversely curved in the form of a spiral as shown in FIG. 14. A radially inner end 179 of the spiral is connected, e.g. formed monolithically with the coupling element 178 of the device. The coupling element itself is reversely curved to house the spiral lower end of the resilient member, which is supported at the upper end of the curved portion at 179. With this construction, the mobility apparatus 170 of the embodiment, and more particularly the device 171 for ground engagement of the apparatus, has increased spring efficiency by increasing the length of the coupling element and active length of the foot anterior to the connection of the coupling element to the foot. This results in a significant spring rate gain in comparison to the device of FIG. 1, for example. Improved spring efficiency enhances the loading response shock absorption and sagittal plane positive kinetic power of the device to aid mobility with ambulation using the apparatus as a walking aid.

The upper end of the shank 175 and the lower end of the hollow staff 13 are telescoped within apertures in the adapter 172 and connected to one another therein by a through bolt 180. See FIG. 17. An elastic member 181 formed of rubber, for example, extends in spaced relation to the upwardly arched midfoot portion 182 of the resilient foot between forefoot portion 183 and hindfoot portion 184 of the foot. The ends of the elastic member are folded over and back onto the ends of the forefoot and hindfoot and secured to the proximal surfaces of the foot by adhesive such as an epoxy glue. Alternatively a hook and loop fastener such as Velcro could be provided to removably connect the ends of the elastic member to the foot. During loading of the mobility assistance apparatus, expansion of the upwardly arched midfoot portion 182 of the foot tensions the elastic member 181 which stores energy that is subsequently released during force unloading to aid propulsion with ambulation using the apparatus as a walking aid. The distal surface of the elastic member has tread 185 thereon and serves a sole of the foot of the device.

The device 171 further comprises a posterior calf device 186 extending between the upper end of the shank and a lower portion of the device, e.g., the lower end of the shank/upper end of the coupling element. The posterior calf device includes an elastic band 187 of latex rubber, for example, extending between a support post 188 on the posterior side of the adapter 172 connected to the upper end of the shank, and a lower portion of the device. Instead of an elastic band, other energy storing means such as an artificial muscle as disclosed in the aforementioned, commonly owned International Application No. PCT/US05/011292 could be used in the posterior calf device as the elastic member. A loop of material 189, such as nylon, extending through the spacing 190 between the lower end of the shank and the surrounding coupling element supports the lower end of the elastic band on the device. The elastic band is preferably in a tensioned condition on the device. Alternatively, an ankle hook monolithically formed with the device as shown at 210 in FIG. 24 can be provided for securing the lower end of the elastic band.

Anterior motion of the upper end of the shank during ambulation and expansion of the anterior facing convexly curved shank result in expansion of the elastic band to store energy during force loading. The stored energy is released during force unloading to generate propulsive force to aid mobility with ambulation using the apparatus as a walking aid.

Figure 18:
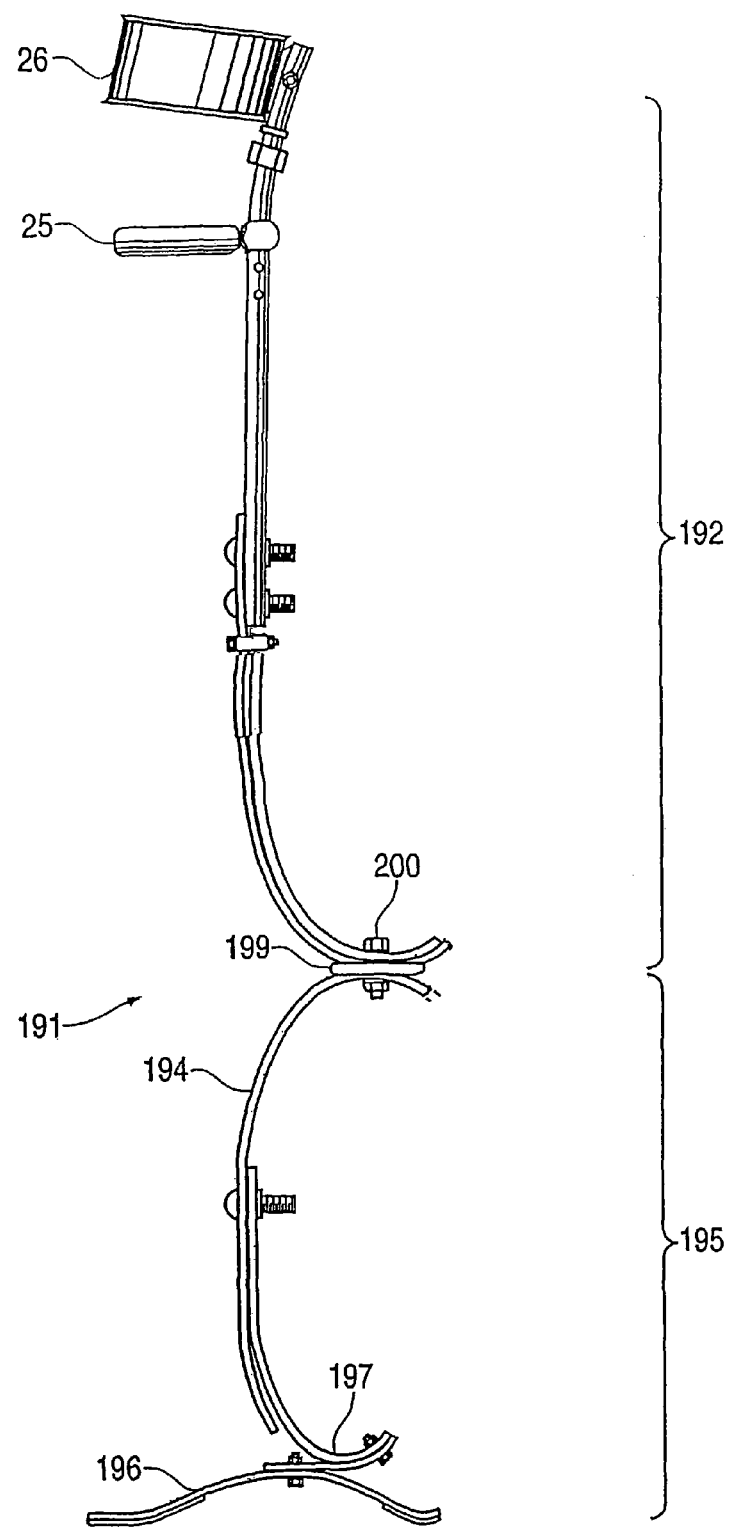
FIG. 18 is a side view of a further embodiment of a forearm crutch of the invention wherein the support of the apparatus located above the device for ground engagement is not only capable of bearing vertical forces during use of the apparatus as a walking aid, but also is formed as a resilient anterior facing convexly curved support which flexes under load during use to store and release energy to aid mobility during ambulation using the crutch.
Figure 21:
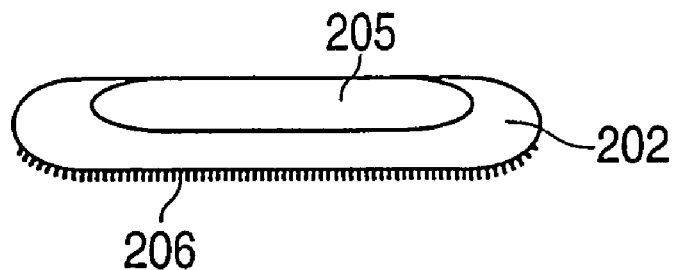
FIG. 21 is an elevation view from one side and above of one slipper sock of a set of slipper socks depicted in FIGS. 21-23 for the foot of the apparatus, steel spikes being provided on the distal surface of the slipper sock for use on ice.
Figure 22:
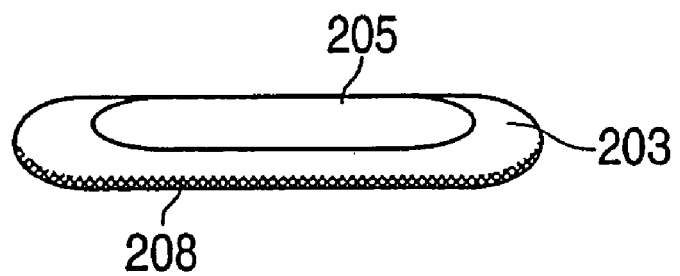
FIG. 22 is a elevation view from one side and above of another slipper sock of the set of slipper socks for the foot of the apparatus, with a mud tread being provided on the distal surface of the slipper sock.
Figure 23:
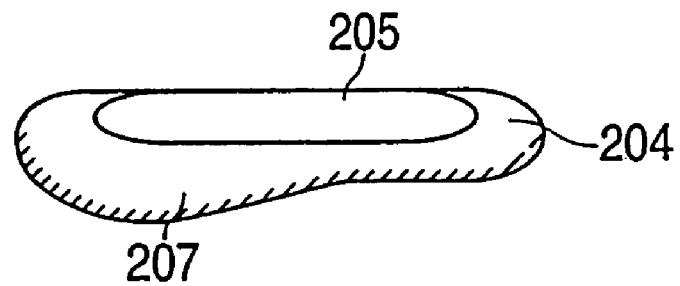
FIG. 23 is an elevation view from one side and above of a further slipper sock of the set of slipper socks, with a large snowshoe area being provided on the distal surface of the slipper sock.
Figure 24:
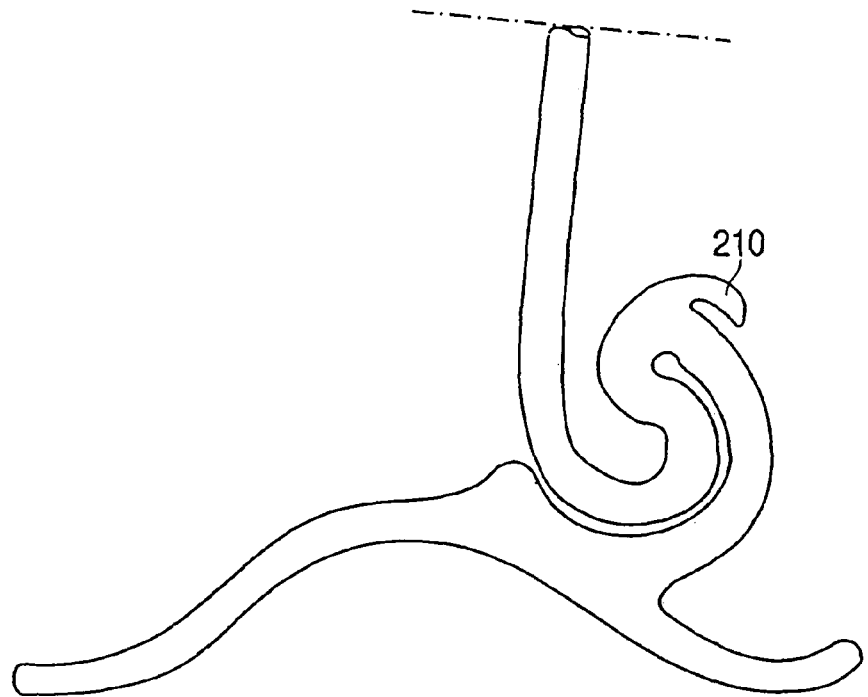
FIG. 24 is a side view of a device for ground engagement in the apparatus of FIGS. 14-17 wherein an ankle hook is monolithically formed on the device to retain a lower end of a posterior calf device.

The forearm crutch 191 in the embodiment of FIGS. 18-20 comprises a support 192 capable of bearing vertical forces during use of the apparatus as a walking aid. The support 192, instead of being a straight, rigid, hollow staff like that at 13 in the previous embodiments, is a resilient, curvilinear support which flexes to store energy during force loading and release stored energy during force unloading to aid mobility. In the example embodiment, the resilient support 192 is anterior facing convexly curved over at least most of the height of the support. More particularly, the support includes a curvilinear thigh shank 193 connected to an upper end of the shank 194 of device 195 for ground engagement.

The device 195 includes a resilient foot 196, ankle 197 and the shank 194 which, like the devices in the previous embodiments, store energy during force loading and release stored energy during force unloading to generate forward propulsive force to aid mobility with ambulation using the apparatus as a walking aid. A handgrip 25 and forearm support 26 are connected to the upper end of the curvilinear thigh shank 193. The components of the device 195 and thigh shank 193 are formed of flexible aluminum members in the example embodiment but other materials could be used as will be apparent to the skilled artisan. The thigh shank is connected to the upper end of the shank 194 by way of a coupling 199 and threaded fastener 200.

Each of the shanks in the crutch 191 could be provided with a posterior calf device, not shown, like those previously described for storing additional energy during loading to aid mobility during force unloading. Similarly, the resilient foot 196 could be provided with an elastic member connecting plantar posterior and anterior portions of the foot to store energy during force loading of the apparatus and release stored energy during force unloading to aid propulsion with ambulation using the apparatus as a walking aid. For example, an elastic member like that at 181 in FIG. 14, or an artificial muscle as referred to above, could be provided on the foot of the embodiment in FIGS. 18-20. As noted above, the ankle and shank of the apparatus of the invention allow the crutch user to advance their body's center of mass forward of the foot. As this occurs, the crutch tip longitudinal arch, ankle and shank load with elastic potential energy. This energy is returned as kinetic power, which is needed to do the work of walking. The consequence of this kinetic power is an increase in crutch user linear gait speed with less energy expended.

According to a further feature of the invention, the mobility assistance apparatus in each of the disclosed embodiments can be used, in combination, with a set of various terrain foot slipper socks for the apparatus. In the example embodiment the set includes slipper socks 202, 203 and 204 shown respectively in FIGS. 21-23. Each of the slipper socks has an opening 205 in its upper end to permit the foot of the device to be inserted with tensioning of the slipper sock on the foot to removably retain the slipper sock on the device during use. The slipper sock 202 has steel spikes 206 on its bottom surface for use on ice. The slipper sock 204 of FIG. 23 has a larger, snowshoe surface area 207 for use on snow. The slipper sock 203 of FIG. 22 has a mud tread 208 formed on a slower surface. Crutch ambulators walk on many different ground surfaces including ice, snow, mud, etc. With the set of various terrain foot slipper socks and the mobility assistance apparatus of the invention, the user can select the appropriate slipper sock dependent upon the inclement weather surface to be navigated. Once indoors, the user can remove the slipper sock and utilize the tread that exists on the foot of the device. Many different distal surface configurations for different ground surfaces could be provided in the set as will be apparent to the skilled artisan.

Figure 25:
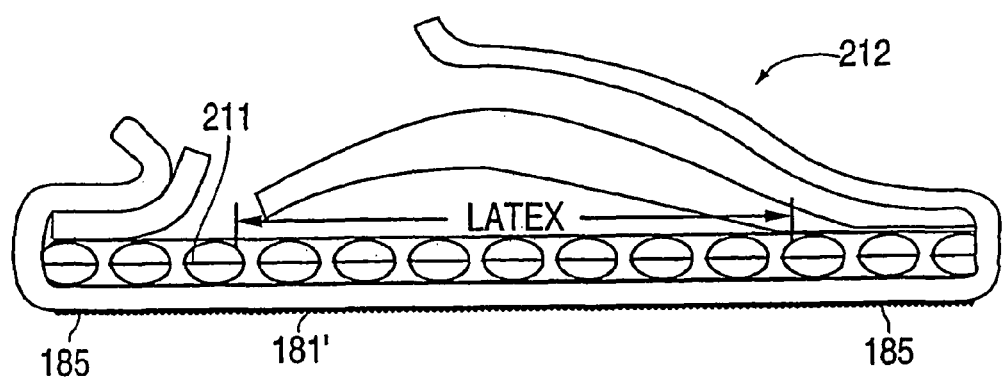
FIG. 25 is a side view, partially in cross section, of the lower end of another form of device for ground engagement in an apparatus of the invention, the device having a distal sole with oyster springs for shock absorption, the distal sole having tread and being formed of an elastic material which is tensioned on force loading during use to store energy for release to aid mobility.

A further feature of the invention involves providing small oyster springs, 211 in FIG. 25, in the toe and heel distal surfaces of the elastic member 181 of device 212 for ground engagement to further cushion shocks and improve efficiency of the apparatus. The device 212 is otherwise constructed like device 171 in FIG. 14.

Figures 26, 27, 28:
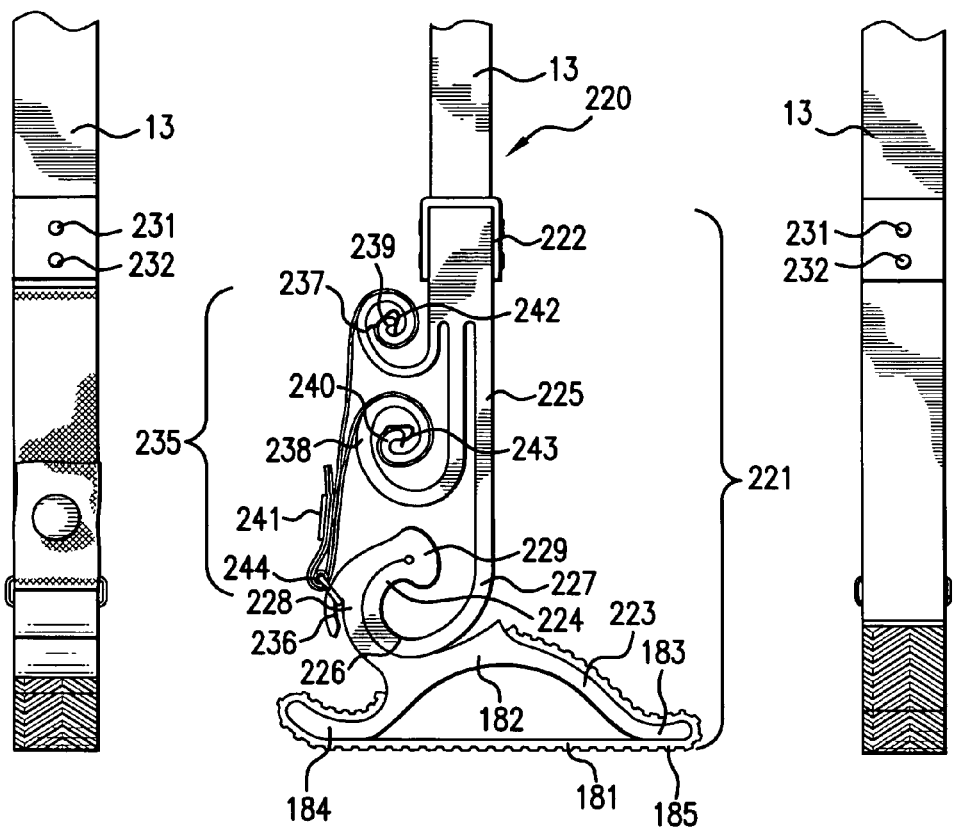
FIG. 26 is a side view of the lower portion of a further embodiment of a crutch according to the invention, including a device for ground engagement forming the crutch tip connected by way of an adapter to the lower end of a hollow staff as in the embodiments of FIGS. 1 and 14.
FIG. 27 is a front view of the mobility assistance apparatus of FIG. 26, as seen from the right side of FIG. 26.
FIG. 28 is a rear view of the crutch of FIG. 26, as seen from the left side of FIG. 26.

FIGS. 26-28 depict the lower end of a forearm crutch 220 wherein a device 221 for ground engagement in the form of prosthetic foot is connected to the lower end of a hollow staff 13 of the crutch by way of an adapter 222. The hollow staff at its upper end has a hand grip and forearm support, not shown, like those in the embodiment of FIG. 1. The device 221 includes a resilient foot 223, ankle 224 and shank 225 which, as described above with respect to previous embodiments, flex to store energy during force loading and release stored energy during force unloading to generate forward propulsive force to aid mobility with ambulation using the apparatus 220 as a walking aid. The ankle and shank are formed by a resilient member having a reversely curved lower end 226 secured to the foot to form the ankle and extending upward from the foot by way of an anterior facing convexly curved portion 227 of the member. The resilient member is secured to the foot by way of a coupling element 228 which houses the reversely curved lower end of the member.

The lower end 226 of the resilient member forming the ankle and shank is reversely curved in the form of a spiral as shown in FIG. 26. A radially inner end 229 of the spiral is connected, e.g. formed monolithically with the coupling element 228 of the device. The coupling element itself is reversely curved to house the spiral lower end of the resilient member, which is supported at the upper end of the curved portion at 229. With the construction, the mobility apparatus 220 of the embodiment, and more particularly the device 221 for ground engagement of the apparatus, has increased spring efficiency by increasing the length of the coupling element and active length of the foot anterior to the connection of the coupling element to the foot as in the embodiment of FIGS. 14-17. This results in a significant spring rate gain in comparison to the device of FIG. 1, for example. Improved spring efficiency enhances the loading response shock absorption and sagittal plane positive kinetic power of the device to aid mobility with ambulation using the apparatus as a walking aid as discussed above.

Figure 29:
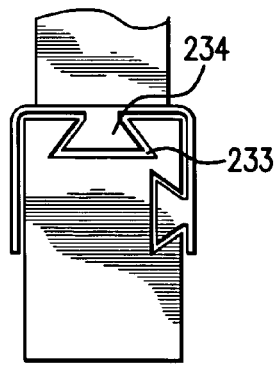
FIG. 29 is a side view of a connection fitting of an adapter for connecting the device for ground engagement to the lower end of the hollow shaft of the crutch of FIGS. 26-28.

The upper end of the shank 225 and the lower end of the hollow staff 13 can be telescoped within apertures in an adapter 172 and connected to one another therein by a through bolt 180 as shown in the embodiment of FIG. 14-17. Alternatively, as shown in FIGS. 26-28, an adapter 222 in the form of a U-shaped connection fitting receives the proximal end of the shank 225 and is held therein by fasteners 231 and 232 such as rivets which extend through holes formed in the end of the shank. In a variation of this, as shown in FIG. 29, cooperating undercut dovetail grooves 233 and complimentarily shaped projections 234 received in the grooves can be formed on respective ones of the proximal end of the shank and the connection fitting. The groove and projections formed on top, bottom and side facing surfaces of the shank and connection fitting are generally triangular/trapezoidal shaped but other shapes and arrangements for the dovetail connections could be employed. The connection fitting 222 is made of metal in the embodiment and is connected to the lower end of the hollow staff by welding. However, as a variation of this construction, a tubular device could be attached to the top of the connection fitting for releasably accepting the distal aspect of the forearm crutch hollow staff 13 as in the embodiments in FIGS. 1-3 and 14-17, for example.

As in the embodiment of FIGS. 14-17, elastic member 181 formed of rubber, for example, extends in spaced relation to the upwardly arched midfoot portion 182 of the resilient foot 223 between the forefoot portion 183 and hindfoot portion 184 of the foot. The ends of the elastic member are folded over and back onto the ends of the forefoot and hindfoot and secured to the proximal surfaces of the foot by adhesive such as an epoxy glue. Alternatively a hook and loop fastener such as Velcro could be provided to removably connect the ends of the elastic member to the foot. During loading of the mobility assistance apparatus, expansion of the upwardly arched midfoot portion 182 of the foot tensions the elastic member 181 which stores energy that is subsequently released during force unloading to aid propulsion with ambulation using the apparatus as a walking aid. The distal surface of the elastic member has tread 185 thereon and serves as a sole of the foot of the device.

The device 221 further comprises a posterior calf device 235 extending between the upper end of the shank and a lower portion of the device, e.g., an ankle hook 236 formed on the coupling element 228. The posterior calf device includes two coiled springs 237 and 238. Each spring has a radially inner, free end, 239 and 240, supported at an upper portion of the device, above the ankle 224, for movement with the shank. A flexible, elongated member 241, such as a nylon strap, is connected at respective ends of the member by way of hook shaped metal connectors 242 and 243 to the inner, free ends of the coil springs and extends over the coil springs. The ends of the hook connectors fit over the free ends of the coiled springs. An intermediate portion of the elongated member passes about a return 244 in the form of a metal ring/loop supported on the ankle hook 236.

When the crutch is force loaded and dorsiflexed in use, the upper end of the shank moves anteriorly relative to the foot and tensions/further tensions strap 241 which resiliently expands the coiled springs. In the mid to late phases of gait the two coiled springs resiliently uncoil. The device 221 functions like an eccentrically contracting muscle. Thus, the coiled springs store energy with force loading of the apparatus during use and release their stored energy during force unloading to generate propulsive force to aid mobility.

In the example embodiment, the resilient member forming the ankle and shank, the coupling element, the foot and the two coiled springs on the shank are preferably monolithically formed by extrusion of a plastic material such as copolymer. Alternatively, the monolithically formed device 221 could be formed by other methods including molding, machining and/or casting, and using other materials, for example metal, carbon nanotubes, epoxy laminated carbon Kevlar and/or fiberglass to construct the device.

In accordance with another feature of the invention, the coiled springs of the posterior calf device 235 can be made wider and thicker and/or narrower and thinner than the ankle, shank and foot resilient structures to provide the resilient device 221 of the forearm crutch with a dorsiflexion moment which is an order of magnitude greater than a plantarflexion moment of the device. Preferably the resilient mass of the two coiled springs is made to create a ratio of the dorsiflexion moment of the device to the plantarflexion moment of the device on the order of 11:1 to resemble the human below knee complex dorsiflexion to plantarflexion moment ratio to aid mobility of a person using the forearm crutch. All the mobility assistance devices as shown in FIGS. 1-29 are wider in the frontal plane than they are thick in the sagittal plane. However, as will be apparent to the skilled artisan, the devices could also be made narrower in the frontal plane than they are thick in the sagittal plane, and/or square.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. The apparatus of the invention is useful in other walking aids, such as canes, walkers, and other types of crutches than the forearm crutches in the example embodiments. More particularly, reasonable variations and modifications are possible in the component parts and/or arrangements of the subject combination arrangement within the scope of the foregoing disclosure, the drawings, and the appended claims without departing from the spirit of the invention. Variations in materials of construction, and the length, width and thickness of the components of the mobility assistance apparatus are also envisioned. Also, in addition to variations and modifications in the component parts and/or arrangements, alternative uses will also be apparent to those skilled in the art.

We claim:

1. A mobility assistance apparatus comprising:
a walking aid;
a resilient device connected to a lower portion of the walking aid for ground engagement, the device including a resilient foot, a resilient ankle and a resilient substantially vertically oriented shank having a dynamic response characteristic to forces associated with ambulating using the apparatus as a walking aid which generates propulsive force to aid mobility;
wherein the device includes at least one coiled spring which is situated posteriorly on the shank above the ankle, said shank and the at least one coiled spring being wider in width than thick front to back, the coiled spring having a radially inner, free end and a radially outer end supported at an upper portion of the shank for movement therewith, and at least one flexible, elongated member connected to the radially inner, free end of the coiled spring and extending over the coiled spring to a lower posterior portion of the device for resiliently expanding the coiled spring in the midstance phase of gait to store energy with force loading of the apparatus during use and to release stored energy during force unloading to generate propulsive force to aid mobility.

2. The mobility assistance apparatus according to claim 1, wherein the walking aid is selected from the group consisting of a crutch and a cane.

3. The mobility assistance apparatus according to claim 1, wherein the at least one coiled spring is monolithically formed with the shank.

4. The mobility assistance apparatus according to claim 1, wherein the resilient device includes two coiled springs on the shank, each spring having a radially inner, free end and a radially outer end supported at an upper portion of the shank, and wherein at least one flexible, elongated member is connected to the radially inner, free end of each of the coiled springs and extends over the coiled springs to a lower portion of the device for resiliently expanding the coiled springs to store energy with force loading of the apparatus during use and to release stored energy during force unloading to generate propulsive force to aid mobility.

5. The mobility assistance apparatus according to claim 4, wherein a common flexible, elongated member is connected at respective ends thereof to the radially inner, free ends of the two coiled springs, an intermediate portion of the common elongated member passing about a return at the lower portion of the device.

6. The mobility assistance apparatus according to claim 4, wherein the two coiled springs are each monolithically formed with the shank.

7. The mobility assistance apparatus according to claim 1, wherein the resilient device has a dorsiflexion moment which is an order of magnitude greater than a plantarflexion moment of the device.

8. The mobility assistance apparatus according to claim 7, wherein the ratio of the dorsiflexion moment of the device to the plantarflexion moment of the device is on the order of 11:1.

9. The mobility assistance apparatus according to claim 1, wherein a connection between the lower portion of the walking aid and a proximal end of the resilient device includes a connection fitting, cooperating undercut grooves and complimentarily shaped projections received in the grooves being provided on respective ones of the proximal end of the device and the connection fitting for forming the connection.

10. The mobility assistance apparatus according to claim 9, wherein the connection fitting includes a proximal tubular receptacle receiving a distal aspect of the walking aid.

11. The mobility assistance apparatus according to claim 1, wherein the resilient foot, the ankle, the shank and the at least one coiled spring are monolithically formed.

12. The mobility assistance apparatus according to claim 1, further comprising an ankle hook monolithically formed with the ankle for securing the at least one elongated member to the lower portion of the device.

13. The mobility assistance apparatus according to claim 1, wherein the ankle and the shank are formed by a resilient member having a reversely curved lower end secured to the foot to form the ankle and extending upward from the foot by way of an anterior facing convexly curved portion of the member to an upper end above the ankle to form the shank, and wherein the resilient member is secured to the foot by way of a coupling element which houses the reversely curved lower end of the member.

14. The mobility assistance apparatus according to claim 13, wherein the resilient member, coupling element, foot and at least one coiled spring are monolithically formed.

15. A mobility assistance apparatus comprising:
a walking aid including a support capable of bearing vertical forces during use of the apparatus;
a resilient device connected to a lower portion of the support for ground engagement, the device having a dynamic response characteristic to forces associated with ambulating using the apparatus as a walking aid which generates propulsive force to aid mobility;
wherein the device includes two coiled springs, each spring having a radially inner, free end and a radially outer end supported at an upper portion of the device for movement therewith, and a flexible, elongated member connected at respective ends thereof to the inner, free ends of the two coiled springs, an intermediate portion of the elongated member passing about a return at a lower portion of the device for resiliently expanding the coiled springs to store energy with force loading of the apparatus during use and to release stored energy during force unloading to generate propulsive force to aid mobility;

wherein the walking aid is selected from the group consisting of a crutch and a cane.

16. The mobility assistance apparatus according to claim 15, wherein the two coiled springs are each monolithically formed with the resilient device.

17. The mobility assistance apparatus according to claim 15, wherein the resilient device has a dorsiflexion moment which is an order of magnitude greater than a plantarflexion moment of the device.

18. The mobility assistance apparatus according to claim 15, wherein a connection between the lower portion of the support and a proximal end of the resilient device includes a connection fitting, cooperating undercut grooves and complimentarily shaped projections received in the grooves being provided on respective ones of the proximal end of the device and the connection fitting for forming the connection.

19. A mobility assistance apparatus comprising:
a support capable of bearing vertical forces during use of the apparatus as a walking aid;
a resilient device connected to a lower portion of the support for ground engagement, the device having a dynamic response characteristic to forces associated with ambulating using the apparatus as a walking aid which generates propulsive force to aid mobility;
wherein the device includes on an upper portion thereof at least one coiled spring situated posteriorly on the device and having a radially inner, free end and a radially outer end supported at the upper portion of the device for movement therewith, the at least one coiled spring being wider in width than thick front to back, and a flexible, elongated member connected to the radially inner free end of the coiled spring and extending over the coiled spring to a lower posterior portion of the device for resiliently expanding the coiled spring in the midstance phase of gait to store energy with force loading of the apparatus during use and to release stored energy during force unloading to generate propulsive force to aid mobility.

20. The mobility assistance apparatus according to claim 19, wherein the at least one coiled spring is monolithically formed with the resilient device.

* * * * *